(12) United States Patent
Matsumoto et al.

(10) Patent No.: US 7,812,025 B2
(45) Date of Patent: Oct. 12, 2010

(54) BRAIN/NEURONAL CELL-PROTECTING AGENT AND THERAPEUTIC AGENT FOR SLEEP DISORDER

(75) Inventors: Takahiro Matsumoto, Osaka (JP); Masakuni Kori, Osaka (JP); Mitsunori Kouno, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 138 days.

(21) Appl. No.: 11/990,385

(22) PCT Filed: Aug. 11, 2006

(86) PCT No.: PCT/JP2006/315936
§ 371 (c)(1),
(2), (4) Date: Feb. 11, 2008

(87) PCT Pub. No.: WO2007/020888
PCT Pub. Date: Feb. 22, 2007

(65) Prior Publication Data
US 2009/0048263 A1    Feb. 19, 2009

(30) Foreign Application Priority Data
Aug. 12, 2005   (JP)   ............... 2005-234313

(51) Int. Cl.
| | | |
|---|---|---|
| A61K 31/501 | (2006.01) | |
| A61K 31/497 | (2006.01) | |
| A61K 31/44 | (2006.01) | |
| C07D 237/02 | (2006.01) | |
| C07D 401/06 | (2006.01) | |
| C07D 403/06 | (2006.01) | |
| C07D 413/06 | (2006.01) | |
| C07D 241/06 | (2006.01) | |
| C07D 401/02 | (2006.01) | |
| C07D 213/02 | (2006.01) | |

(52) U.S. Cl. ................. 514/252.01; 514/252.02; 514/253.01; 514/253.13; 514/336; 514/352; 544/224; 544/238; 544/360; 544/366; 544/367; 544/399; 546/256; 546/265

(58) Field of Classification Search ............ 514/252.02, 514/253.01, 253.1, 254.04, 252.01, 253.13, 514/336, 352; 544/238, 360, 364, 367, 224, 544/366, 399; 546/256, 265
See application file for complete search history.

(56) References Cited

U.S. PATENT DOCUMENTS

| 6,432,947 B1 | 8/2002 | Arnaiz et al. |
| 2002/0019389 A1 | 2/2002 | Kim et al. |
| 2003/0092734 A1 | 5/2003 | Boger |

FOREIGN PATENT DOCUMENTS

| EP | 0 519 449 | 12/1992 |
| HU | 9903870 | * 5/2000 |
| JP | 62-089679 | 4/1987 |
| JP | 11-139969 | 5/1999 |
| WO | WO 88/08424 | 11/1988 |
| WO | WO 96/01820 | 2/1996 |
| WO | WO 96/21648 | 7/1996 |
| WO | WO 96/33994 | 10/1996 |
| WO | WO 98/00402 | 1/1998 |
| WO | WO 98/06745 | 2/1998 |
| WO | WO 98/37079 | 8/1998 |
| WO | WO 00/52001 | 9/2000 |
| WO | WO 01/66551 | 9/2001 |
| WO | WO 02/05819 | 1/2002 |

(Continued)

OTHER PUBLICATIONS

Kenneth et al., Synthesis and evaluation of Pyridazinylpiperazines as vanilloid receptor 1 antagonists; Bioorganic & Medicinal Chemistry Letters (2004), 14(22), 5513-5519.*

(Continued)

*Primary Examiner*—James O Wilson
*Assistant Examiner*—Ebenezer Sackey
(74) *Attorney, Agent, or Firm*—Hamre, Schumann, Mueller & Larson, P.C.

(57) ABSTRACT

A compound represented by the formula (I) or a salt thereof; and an agent for protecting a brain/neuronal cell or a therapeutic agent for sleep disorder comprising the compound or salt: wherein Z represents an oxygen or sulfur; $R^1$ represents an aryl or heterocyclic group which may be substituted, provided that $R^1$ is not a 3-ethyl-6-methoxy-2-methyl-5-naphthalen-1-yl group; $R^{1a}$ represents a hydrogen atom, a hydrocarbon group which may be substituted, a hydroxyl group or the like; $R^2$ represents a piperidin-1,4-diyl or piperazin-1,4-diyl which may be substituted; $R^3$ represents a bivalent group which is formed by removing two hydrogen atoms from a benzene ring or 6-membered aromatic heterocyclic ring which may have a substituent, provided that $R^3$ is not a pyridazin-3,6-diyl; and $R^4$ represents a group which is formed by removing one hydrogen atom from a benzene ring or 5- to 6-membered heterocyclic ring which may be substituted, provided that the substituent on the heterocyclic ring is not a phenylethyl group which may be substituted when Z is sulfur.

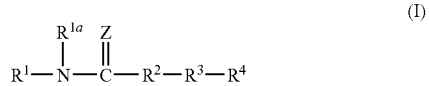

(I)

11 Claims, No Drawings

FOREIGN PATENT DOCUMENTS

| | | |
|---|---|---|
| WO | WO 02/083134 | 10/2002 |
| WO | WO 03/045313 | 6/2003 |
| WO | WO 03/062234 | 7/2003 |
| WO | WO 03/064386 | 8/2003 |
| WO | WO 03/080060 | 10/2003 |
| WO | WO 2004/018439 | 3/2004 |
| WO | WO 2004018439 * | 3/2004 |
| WO | WO 2004/056772 | 7/2004 |
| WO | WO 2004/058732 | 7/2004 |
| WO | WO 2004/099164 | 11/2004 |
| WO | WO 2005/021548 | 3/2005 |
| WO | WO 2005/036169 | 4/2005 |
| WO | WO 2006/058338 | 6/2006 |

OTHER PUBLICATIONS

Huang et al. "Synthesis of potent selective serotonin 5-HT1B receptor ligands". *Bioorganic & Medicinal Chemistry Letters*, vol. 15, pp. 4786-4789 (Sep. 2005).

Tafesse et al. "Synthesis and evaluation of pyridazinylpiperazines as vanilloid receptor 1 antagonists".*Bioorganic & Medical Chemistry Letters*, vol. 14, pp. 5513-5519 (Sep. 2005).

Fowler et al. "Fatty acid amide hydrolase: biochemistry, pharmacology, and therapeutic possibilities for an enzyme hydrolyzing anandamine, 2-arachidonoylglycerol, palmitoylethanolamide, and oleamide".*Biochemical Pharmacology*, vol. 62, pp. 517-526 (2001).

* cited by examiner

SEQUENCE LISTING

<160> NUMBER OF SEQ ID NOS: 2

<210> SEQ ID NO 1
<211> LENGTH: 36
<212> TYPE: DNA

```
<213> ORGANISM: Artificial
<220> FEATURE:
<223> OTHER INFORMATION: primer

<400> SEQUENCE: 1
aaaagaattc gccaccatgg tgcagtacga gctgtg                                36

<210> SEQ ID NO 2
<211> LENGTH: 27
<212> TYPE: DNA
<213> ORGANISM: Artificial
<220> FEATURE:
<223> OTHER INFORMATION: primer

<400> SEQUENCE: 2
ttttgtcgac tcaggatgac tgctttt                                          27
```

BRAIN/NEURONAL CELL-PROTECTING AGENT AND THERAPEUTIC AGENT FOR SLEEP DISORDER

TECHNICAL FIELD

The present invention relates to a novel brain/neuronal cell-protecting agent, and in particular, to a brain/neuronal cell-protecting agent which is effective in prevention and treatment of cerebrovascular disorders such as cerebral infarction, cerebral hemorrhage and subarachnoid hemorrhage or head injury, or a therapeutic agent for sleep disorders.

BACKGROUND ART

Cerebrovascular disorders are diseases causing an enormous loss in healthcare economy, as they are the second and third most common causes of death in Japan, U.S.A. and Europe as well as the first leading cause of severe sequalae. At present, although active causal treatment is implemented for some patients of cerebral embolism and cerebral thrombosis (e.g., tPA, etc.), the portion of the subject under the benefit is limited to a few percents of the total patients' group, owing to the restriction in therapeutic time window. In most cases, patients are provided only with maintenance therapy for the purpose of preventing cerebral edema and suppressing recurrence and augmentation of the disorder (e.g., antithrombolytic drug), and an effective medicine targeting radical treatment and cerebroprotection is still not available.

It is well recognized that cells of the central nervous system are vulnerable to ischemic stress, and according to basic experiments using a cerebral ischemic model, it is reported that an ischemic state maintained for only a few minutes can cause irreversible impairment and finally death of neuronal cells. It is undeniable that such results have brought about great despair in the clinical field of cerebral stroke. However, in recent years, active research in the realm of neural science has revealed various potential aspects in solving problems such as response to various stresses at the level of individual cells upon ischemic loading, crosstalk between neuronal cells and glial cells, and programmed cell death, and these aspects are highly expected to be linked to the keys to proactive therapeutic strategy. However, although a number of products under development which have various action mechanisms, for example, glutamate antagonist, calcium antagonist, antioxidant and the like have been on trial heretofore, they all failed in the clinical tests. In Japan, Radicut (registered trademark, Mitsubishi Welpharma Kabushiki Kaisha), which is an antioxidant agent, has been approved, but this agent is not yet approved in abroad countries, and a cerebroprotective agent that has been approved worldwide is not available yet.

In association with an improvement in the intensive care system for patients having stroke, brain hypothermia treatment is available as a cerebroprotective therapy, effectiveness of which has been clinically reexamined. The brain hypothermia treatment is based on lowering of the brain temperature (cerebral temperature) to 32 to 35° C. and maintaining at that temperature, and is increasingly getting attention for its remarkable cerebroprotective effect. However, this treatment requires intensive treatment facilities and 24-hour intensive care by a plurality of medical staffs, such that propagation of the treatment as a general therapeutic method is still difficult.

In addition, one of 5 Japanese has some kind of problem with sleep, and users of hypnotics are increasing year by year. Sleep disorders are classified broadly into 4 categories of difficulty in falling asleep and maintaining sleep (insomnia), sleep excess disorder, sleep-wake rhythm disorder, and functional disorder associated with sleep stage or partial awakening (abnormal behavior during sleep). As remedies for insomnia, benzodiazepine receptor agonist is mainly used. However, benzodiazepine receptor agonist has side effects such as motor dysfunction, memory disorder and dependency, thus the development of hypnotics without these side effects has been expected.

Meanwhile, cannabinoid receptors have been identified since 1990's as receptors for Δ9-tetrahydrocannabinol (Δ9-THC), which is an active substance obtained from the hemp plant. At present, the CB1 receptor (see Nature, Vol. 346, p. 561 (1990)), its splice variant CB1a (see J. Biol. Chem., Vol. 270, p. 3726 (1995)), and the CB2 receptor (see Eur. J. Biochem., Vol. 232, p. 54 (1995)) are known. Almost around the same time, N-arachidonoylethanolamine (anandamide), an endogenous ligand for the CB1 receptor, was discovered from the brain of a pig (see Science, Vol. 258, p. 1946 (1992)). Anandamide belongs to the family of N-acylated ethanolamine, as does N-palmitoylethanolamine or N-oleoylethanolamine. Fatty acid amides including these N-acylated ethanolamines are found to have effect on physiological functions such as pain (see Nature, Vol. 394, p. 277 (1998); and Pain, Vol. 76, p. 189 (1998)), dietary regulation (see Nature, Vol. 414, p. 209 (2001)) and promotion of sleep (see Science, Vol. 268, p. 1506 (1995)). The route for biosynthesis or decomposition of fatty acid amides has been investigated since 1980's. First, a calcium-dependent transacylase produces anandamide, which is N-acylphosphatidylethanolamine (see J. Neurochem., Vol. 41, p. 1303 (1983)), and then a fatty acid amide is released therefrom by the action of phospholipase D (see J. Neurochem., Vol. 42, p. 1613 (1984)). The existence of an enzymatic activity which hydrolyzes a fatty acid amide into the corresponding fatty acid, thereby eliminating its physiological activity, was suggested earlier but was confirmed only in the later half of 1990's. An active substance hydrolyzing oleamide was isolated from a rat, and its cDNA was cloned (see Nature, Vol. 384, p. 83 (1996)). The enzyme produced by genetic recombination of the cDNA was able to hydrolyze various fatty acid amides including oleamide and anandamide, and was named as fatty acid amide hydrolase (hereinafter, sometimes abbreviated to "FAAH" in the present specification). Still, it is not sufficiently clear about the enzyme responsible for biosynthesis of fatty acid amides. However, the fact that fatty acid amides are produced from neuronal cells in a calcium-dependent, that is, neuronal activity-dependent manner (see Nature, Vol. 372, p. 686 (1994)), is highly meaningful for development of a therapeutic agent. Furthermore, a FAAH knockout mouse has been produced, and a FAAH inhibitory agent has been discovered, so that the physiological significance of FAAH inhibition is being revealed. In the FAAH knockout mouse, the content of fatty acid amides, including anandamide, in the brain increased by 10 to 15 times, but the mobility, body weight and body temperature of the mouse were normal. However, a decrease in the responsiveness to pain was observed, and this was interrelated to the content of fatty acid amides in the brain (see Proc. Natl. Acad. Sci. USA, Vol. 98, p. 9371 (2001)). For the FAAH inhibitor, trifluoromethyl ketone derivatives (see J. Am. Chem. Soc., 118, 5938 (1996)), alpha-keto heterocyclic ring derivatives (see Proc. Natl. Acad. Sci. USA, Vol. 97, p. 5044 (2000)), sulfonylfluoride derivatives (see Biochem. Biophys. Res. Commun., Vol. 231, p. 217 (1997)), fluorophosphonate derivatives (see Biochem. Pharmacol., Vol. 53, p. 255 (1997)), and arylcarbamate derivatives (see Nat. Med., Vol. 9, p. 76 (2003)) are known.

In addition to this, FAAH or anandamide is reported to be involved with various diseases, and it has been reported that large quantities of FAAH are found in the brain of Alzheimer's patients (see The Journal of Neuroscience, Vol. 23, p. 1136 (2003)). It has been also discovered by a test using rats that an increase in the amount of anandamide results in an antiparkinsonian activity (see Neuropsychopharmacology, Vol. 29, p. 1134 (2004)). It has been also reported that women having miscarriage show decreased levels of FAAH (see J. Clin. Endocrinol. Metab., 89, 5168 (2004)). Anandamide is reported to inhibit propagation of rectal cancer (see Gastroenterology, Vol. 125, p. 677 (2003)). It is reported that an FAAH knockout mouse is not susceptible to colonitis or colitis (see J. Clin. Invest., Vol. 113, p. 1202 (2004)). A FAAH inhibiting drug is reported to exhibit an anxiolytic activity (see Nature Medicine, Vol. 9, p. 76 (2003)). FAAH is reported to be an enzyme hydrolyzing oleylethanolamide, which is a satiety factor present in the small intestine (see Nature, Vol. 414, p. 209 (2001)). FAAH is a hydrolytic enzyme for stearoylethanolamide, and it is reported that administration of stearoylethanolamide to a mouse suppresses eating (see FASEB Journal, Vol. 18, p. 1580 (2004)). Since anandamide is an agonist of the vanilloid receptor, which is a nociceptor, the FAAH inhibitory agent is expected to have the same activity as that of the vanilloid receptor agonist (for example, prophylactic and/or therapeutic activity for frequent urination, urinary incontinence, interstitial cystitis) (see JP 2002-202204 A).

As such, FAAH is reported to be involved with various diseases, but there has been no report to the present, demonstrating the cerebro-neuroprotective effect of FAAH.

Since FAAH is an enzyme which hydrolyzes an endogenous sleep substance: oleamide, a FAAH inhibitory agent suppresses the decomposition of oleamide to induce sleep (US 2003/0092734 A).

In addition, as a compound represented by the formula (I):

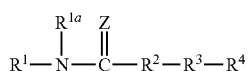

(I)

wherein Z represents an oxygen or a sulfur, $R^1$ represents an optionally substituted aryl, or an optionally substituted heterocyclic group, $R^{1a}$ represents a hydrogen atom, an optionally substituted hydrocarbon group, hydroxy, an optionally substituted alkoxy, an optionally substituted aryloxy, an optionally substituted amino, or a 5- to 7-membered saturated cycloamino which may be substituted, $R^2$ represents an optionally substituted piperidin-1,4-diyl or an optionally substituted piperazin-1,4-diyl, $R^3$ represents a divalent group formed by removing two hydrogen atoms from an optionally substituted 6-membered ring, and $R^4$ represents a group formed by removing one hydrogen atom from an optionally substituted benzene ring or an optionally substituted 5- to 6-membered heterocyclic ring containing 1 to 4 heteroatoms selected from oxygen atom, sulfur atom and nitrogen atom in addition to carbon atom, for example, (a) WO 2004/099164 discloses 2,2-dichloro-N-[3-[3-[2-chloro-6-(4-phenylcarbamoylpiperazino)phenyl]-5-isoxazolyl]phenyl]acetamide, (b) Bioorganic & Medicinal Chemistry Letters (2004), 14(22), 5513-5519 discloses a compound wherein $R^3$ is pyridazin-3,6-diyl, (c) WO 2003/045313 discloses a compound wherein $R^1$ is an optionally substituted quinolyl, (d) WO 2002/083134 discloses a compound wherein $R^2$ is piperidin-1,4-diyl substituted with cyclopropylmethylaminomethyl, (e) U.S. Pat. No. 6,432,947 and WO 9837079 disclose a compound wherein $R^2$ is piperazin-1,4-diyl substituted with an optionally substituted carbamoyl or an optionally substituted carbamoylmethyl, respectively, (f) WO 2002/005819 discloses 4-biphenyl-4-yl-N-{3-[2-(diisopropylamino)ethoxy]-4-methoxyphenyl}-3-methylcyclohexanecarboxamide, (g) WO 2001/066551 discloses a compound wherein $R^4$ is a group formed by removing one hydrogen atom from a 5- to 6-membered heterocyclic ring substituted with 2-(2,4-difluorophenyl)-2-hydroxy-3-(1H-1,2,4-triazol-1-yl)propyl and 1-(4-chlorobenzoyl)propyl, (h) WO 2000/052001 discloses 4-biphenyl-2-yl-N-(3-methoxy-5,8-dihydroquinoxaline-2-yl)piperazine-1-carboxamide, (i) WO 98/00402 discloses 4-(4-methoxybiphenyl-3-yl)-N-(2-methoxy-4,5-dimethylphenyl)piperazine-1-carboxamide, (j) WO 96/21648 discloses a compound wherein $R^1$ is 5-ethyl-2-methoxy-6-methyl-3-pyridinyl, (k) WO 96/01820 discloses a compound wherein the group formed by removing one hydrogen atom from an optionally substituted benzene ring or an optionally substituted 5- to 6-membered heterocyclic ring containing 1 to 4 heteroatoms selected from oxygen atom, sulfur atom and nitrogen atom in addition to carbon atom, represented by $R^4$, is 1-(4-chlorobenzoyl)propyl-1,5-dihydro-5-oxo, and (l) JP-A 62-89679 discloses 1-[4-(4,5-dihydrofuran-2-yl)phenyl]-N-pyridin-4-ylpiperidine-4-carboxamide.

However, these documents have no description that these compounds are a FAAH inhibitor.

DISCLOSURE OF THE INVENTION

Problem to be Solved by the Invention

Currently, the treatment of cerebrovascular disorders in most cases need to be carried out only after obtaining a confirmatory diagnosis such as a diagnosis using X-ray, CT or MRI imaging, and thus the therapeutic time window is limited thereby. Accordingly, establishment of a novel prophylactic and/or therapeutic means for cerebrovascular disorders, which is not selective on the disease type and does not require confirmatory diagnosis, is highly demanded. Furthermore, as a therapeutic agent for sleep disorder, development of therapeutic agent is highly desired that is different from benzodiazepine receptor agonist and enhances natural sleep.

An object of the present invention is to provide a safe and effective prophylactic or therapeutic agent for cerebrovascular disorders and therapeutic agent for sleep disorder.

Means for Solving the Problem

The present inventors have found, in the course of investigating a variety of drugs for their cerebroprotective effect using a rat cerebral ischemic model so as to achieve the above-described object, that a FAAH inhibitory agent markedly reduced infarct volumes of cerebral ischemic rats, and thus found that a fatty acid amide hydrolase inhibitory agent is effective for prevention and treatment of neural disorders, in particular, of cerebrovascular disorders such as cerebral infarction, cerebral hemorrhage and subarachnoid hemorrhage, or head injury. Furthermore, the present inventors have found that a compound represented by the following formula (I) and formula (I') which is included in the scope of formula (I), or a salt thereof (hereinafter, sometimes, referred to as Compound (I) and Compound (I'), respectively) has a FAAH inhibitory activity and is useful as a brain/neuronal cell-protecting agent, and further that Compound (I) and (I') are useful as a prophylactic or therapeutic agent for sleep disorders, thus the present invention has been completed. In addition, the Compound (I) is a novel compound. In the present specification, sometimes, Compound (I) and Compound (I') are collectively referred to as the compound of the present invention.

Thus, the present invention provides:

(1) A compound represented by the formula (I):

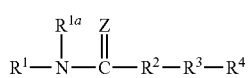

wherein Z represents an oxygen or sulfur, $R^1$ represents an optionally substituted aryl or an optionally substituted heterocyclic group (provided that an optionally substituted quinolyl and 5-ethyl-2-methoxy-6-methyl-3-pyridinyl are excluded), $R^{1a}$ represents a hydrogen atom, an optionally substituted hydrocarbon group, hydroxy, an optionally substituted alkoxy, an optionally substituted aryloxy, an optionally substituted amino or an optionally substituted 5- to 7-membered saturated cyclic amino, $R^2$ represents an optionally substituted piperidin-1,4-diyl or an optionally substituted piperazin-1,4-diyl (provided that those substituted with propylaminomethyl, dipropylaminomethyl, cyclopropylmethylaminomethyl, dicyclopropylmethylaminomethyl, a substituted carbamoyl or a substituted carbamoylmethyl are excluded), $R^3$ represents a divalent group formed by removing two hydrogen atoms from an optionally substituted 6-membered ring (provided that pyridazin-3,6-diyl is excluded), and $R^4$ represents a group formed by removing one hydrogen atom from an optionally substituted benzene ring or an optionally substituted 5- to 6-membered heterocyclic ring containing 1 to 4 heteroatoms selected from oxygen atom, sulfur atom and nitrogen atom in addition to carbon atom (provided that 1-[2-(2,4-difluorophenyl)-2-hydroxy-3-(1H-1,2,4-triazol-1-yl)propyl]-5-oxo-1,5-dihydro-4H-1,2,4-triazol-4-yl and 1-[1-(4-chlorobenzoyl)propyl]-5-oxo-1,5-dihydro-4H-1,2,4-triazol-4-yl are excluded, and the substituent of the heterocyclic ring does not have phenyl group), provided that 4-biphenyl-2-yl-N-(3-methoxy-5,8-dihydroquinoxaline-2-yl)piperazine-1-carboxamide, 4-(4-methoxybiphenyl-3-yl)-N-(2-methoxy-4,5-dimethylphenyl)piperazine-1-carboxamide, 1-[4-(4,5-dihydrofuran-2-yl)phenyl]-N-pyridin-4-ylpiperidine-4-carboxamide, 2,2-dichloro-N-[3-[3-[2-chloro-6-(4-phenylcarbamoylpiperazino)phenyl]-5-isoxazolyl]phenyl]acetamide, 1-[(2-methoxyquinolin-3-yl)aminocarbonyl]-4-(2-phenyl)piperazine, and 4-[3-(4,6-dimethoxy-2-pyrimidinyloxy)-2-(4,5,6,7-tetrahydrobenzoxazol-2-yl)phenyl]-1-phenylcarbamoylpiperazine are excluded, or a salt thereof;

(2) The compound according to the above-mentioned (1), wherein $R^3$ is a divalent group formed by removing two hydrogen atoms from an optionally substituted benzene ring or an optionally substituted 6-membered aromatic heterocyclic ring containing 1 to 4 heteroatoms selected from oxygen atom, sulfur atom and nitrogen atom in addition to carbon atom, provided that pyridazin-3,6-diyl is excluded, or a salt thereof;

(3) The compound according to the above-mentioned (1), wherein $R^1$ is a $C_{6-10}$ aryl or a 5- to 10-membered heterocyclic group containing 1 to 4 heteroatoms selected from oxygen atom, sulfur atom and nitrogen atom in addition to carbon atom (provided that 5-ethyl-2-methoxy-6-methyl-3-pyridinyl are excluded), each of which may be substituted with one or more substituents selected from a group consisting of a $C_{1-6}$ alkyl which may be halogenated or oxolated, a $C_{1-6}$ alkoxy which may be halogenated or oxolated, a $C_{1-6}$ acylamino which may be halogenated or oxolated, a N—($C_{1-6}$ alkyl)$C_{1-6}$ acylamino, a $C_{1-6}$ acyl which may be halogenated or oxolated, a $C_{1-6}$ alkylamino, a di-$C_{1-6}$ alkylamino, a $C_{1-6}$ alkenyl which may be halogenated or oxolated, a $C_{1-6}$ alkynyl which may be halogenated or oxolated, a $C_{1-6}$ alkyloxycarbonyl, carbamoyl, carboxy, a $C_{1-6}$ alkylsulfonylamide which may be halogenated or oxolated, a $C_{1-6}$ alkylthio which may be halogenated or oxolated, a $C_{1-6}$ alkylsulfinyl which may be halogenated or oxolated, amino, hydroxy, a halogen, nitrile, 2-oxopyrrolidin-1-yl, 2-oxopropyl, imidazolyl and pyrazolyl, $R^{1a}$ is a hydrogen atom, a $C_{1-6}$ aliphatic hydrocarbon group, hydroxy, a $C_{1-6}$ alkoxy, a $C_{6-14}$ aryloxy, amino, a mono-$C_{1-6}$ alkylamino, a di-$C_{1-6}$ alkylamino, or a 5- to 7-membered saturated cyclic amino, $R^2$ is a piperidin-1,4-diyl or a piperazin-1,4-diyl, each of which may be substituted with one or more substituents selected from a group consisting of a $C_{1-6}$ alkyl which may be halogenated or oxolated, a $C_{1-6}$ alkoxy which may be halogenated or oxolated, a $C_{1-6}$ acylamino which may be halogenated or oxolated, a N—($C_{1-6}$ alkyl)$C_{1-6}$ acylamino, a $C_{1-6}$ acyl which may be halogenated or oxolated, a $C_{1-6}$ alkylamino, a di-$C_{1-6}$ alkylamino, a $C_{1-6}$ alkenyl which may be halogenated or oxolated, a $C_{1-6}$ alkynyl which may be halogenated or oxolated, a $C_{1-6}$ alkyloxycarbonyl, carbamoyl, carboxy, a $C_{1-6}$ alkylsulfonylamide which may be halogenated or oxolated, a $C_{1-6}$ alkylthio which may be halogenated or oxolated, a $C_{1-6}$ alkylsulfinyl which may be halogenated or oxolated, amino, hydroxy, a halogen, nitrile, 2-oxopyrrolidin-1-yl and 2-oxopropyl, $R^3$ is a divalent group formed by removing two hydrogen, atoms from benzene ring or a 6-membered aromatic heterocyclic ring (provided that pyridazin-3,6-diyl is excluded), which may have one or more substituents selected from a group consisting of a $C_{1-6}$ alkyl which may be halogenated or oxolated, a $C_{1-6}$ alkoxy which may be halogenated or oxolated, a $C_{1-6}$ acylamino which may be halogenated or oxolated, a N—($C_{1-6}$ alkyl)$C_{1-6}$ acylamino, a $C_{1-6}$ acyl which may be halogenated or oxolated, a $C_{1-6}$ alkylamino, a di-$C_{1-6}$ alkylamino, a $C_{1-6}$ alkenyl which may be halogenated or oxolated, a $C_{1-6}$ alkynyl which may be halogenated or oxolated, a $C_{1-6}$ alkyloxycarbonyl, carbamoyl, carboxy, a $C_{1-6}$ alkylsulfonylamide which may be halogenated or oxolated, a $C_{1-6}$ alkylthio which may be halogenated or oxolated, a $C_{1-6}$ alkylsulfinyl which may be halogenated or oxolated, amino, hydroxy, a halogen, nitrile and 2-oxopropyl, and $R^4$ is a group formed by removing one hydrogen atom from benzene ring or an optionally substituted 5- to 6-membered heterocyclic ring containing 1 to 4 heteroatoms selected from oxygen atom, sulfur atom and nitrogen atom in addition to carbon atom, which may be substituted with one or more substituents selected from a group consisting of a $C_{1-6}$ alkyl which may be halogenated or oxolated, a $C_{1-6}$ alkoxy which may be halogenated or oxolated, a $C_{1-6}$ acylamino which may be halogenated or oxolated, a N—$(C_{1-6}$ alkyl)$C_{1-6}$ acylamino, a $C_{1-6}$ acyl which may be halogenated or oxolated, a $C_{1-6}$ alkylamino, a di-$C_{1-6}$ alkylamino, a $C_{1-6}$ alkenyl which may be halogenated or oxolated, a $C_{1-6}$ alkynyl which may be halogenated or oxolated, a $C_{1-6}$ alkyloxycarbonyl, carbamoyl, carboxy, a $C_{1-6}$ alkylsulfonylamide which may be halogenated or oxolated, a $C_{1-6}$ alkylthio which may be halogenated or oxolated, a $C_{1-6}$ alkylsulfinyl which may be halogenated or oxolated, amino, hydroxy, a halogen, nitrile and 2-oxopropyl;

(4) The compound according to the above-mentioned (1), wherein $R^1$ is phenyl, benzisoxazolyl, isoxazolyl, pyridyl, pyridazinyl, pyrazinyl, pyrimidinyl, or pyrazolyl, each of which may be substituted with one or more substituents selected from a group consisting of a $C_{1-6}$ alkyl which may be halogenated or oxolated, a $C_{1-6}$ alkoxy which may be halogenated or oxolated, a $C_{1-6}$ acylamino which may be halogenated or oxolated, a N—$(C_{1-6}$ alkyl)$C_{1-6}$ acylamino, a $C_{1-6}$ acyl which may be halogenated or oxolated, a $C_{1-6}$ alkylamino, a di-$C_{1-6}$ alkylamino, a $C_{1-6}$ alkenyl which may be halogenated or oxolated, a $C_{1-6}$ alkynyl which may be halogenated or oxolated, a $C_{1-6}$ alkyloxycarbonyl, carbamoyl, carboxy, a $C_{1-6}$ alkylsulfonylamide which may be halogenated or oxolated, a $C_{1-6}$ alkylthio which may be halogenated or oxolated, a $C_{1-6}$ alkylsulfinyl which may be halogenated or oxolated, amino, hydroxy, a halogen, nitrile, 2-oxopyrrolidin-1-yl, 2-oxopropyl, imidazolyl and pyrazolyl;

(5) The compound according to the above-mentioned (1), wherein $R^{1a}$ is hydrogen;

(6) The compound according to the above-mentioned (1), wherein the moiety represented by formula: —C(=Z)—$R^2$— is a divalent group represented by formula:

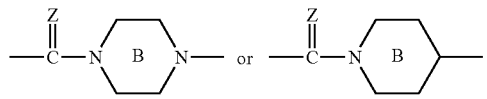

wherein ring B represents piperidine or piperazine, each of which may be substituted with one or more substituents selected from a group consisting of a $C_{1-6}$ alkyl which may be halogenated or oxolated, a $C_{1-6}$ alkoxy which may be halogenated or oxolated, a $C_{1-6}$ acylamino which may be halogenated or oxolated, a N—$(C_{1-6}$ alkyl)$C_{1-6}$ acylamino, a $C_{1-6}$ acyl which may be halogenated or oxolated, a $C_{1-6}$ alkylamino, a di-$C_{1-6}$ alkylamino, a $C_{1-6}$ alkenyl which may be halogenated or oxolated, a $C_{1-6}$ alkynyl which may be halogenated or oxolated, a $C_{1-6}$ alkyloxycarbonyl, carbamoyl, carboxy, a $C_{1-6}$ alkylsulfonylamide which may be halogenated or oxolated, a $C_{1-6}$ alkylthio which may be halogenated or oxolated, a $C_{1-6}$ alkylsulfinyl which may be halogenated or oxolated, amino, hydroxy, a halogen, nitrile, 2-oxopyrrolidin-1-yl and 2-oxopropyl;

(7) The compound according to the above-mentioned (1), wherein $R^3$ is a divalent group represented by formula:

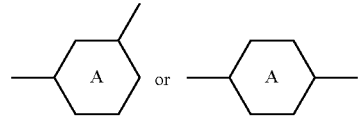

wherein ring A represents benzene ring or a 6-membered aromatic heterocyclic ring, which may have one or more substituents selected from a group consisting of a $C_{1-6}$ alkyl which may be halogenated or oxolated, a $C_{1-6}$ alkoxy which may be halogenated or oxolated, a $C_{1-6}$ acylamino which may be halogenated or oxolated, a N—$(C_{1-6}$ alkyl)$C_{1-6}$ acylamino, a $C_{1-6}$ acyl which may be halogenated or oxolated, a $C_{1-6}$ alkylamino, a di-$C_{1-6}$ alkylamino, a $C_{1-6}$ alkenyl which may be halogenated or oxolated, a $C_{1-6}$ alkynyl which may be halogenated or oxolated, a $C_{1-6}$ alkyloxycarbonyl, carbamoyl, carboxy, a $C_{1-6}$ alkylsulfonylamide which may be halogenated or oxolated, a $C_{1-6}$ alkylthio which may be halogenated or oxolated, a $C_{1-6}$ alkylsulfinyl which may be halogenated or oxolated, amino, hydroxy, a halogen, nitrile and 2-oxopropyl;

(8) The compound according to the above-mentioned (1), wherein $R^3$ is 1,3-phenylene, 1,4-phenylene, pyridin-2,4-diyl or pyridin-2,5-diyl, each of which may have one or more substituents selected from a group consisting of a $C_{1-6}$ alkyl which may be halogenated or oxolated, a $C_{1-6}$ alkoxy which may be halogenated or oxolated, a $C_{1-6}$ acylamino which may be halogenated or oxolated, a N—$(C_{1-6}$ alkyl)$C_{1-6}$ acylamino, a $C_{1-6}$ acyl which may be halogenated or oxolated, a $C_{1-6}$ alkylamino, a di-$C_{1-6}$ alkylamino, a $C_{1-6}$ alkenyl which may be halogenated or oxolated, a $C_{1-6}$ alkynyl which may be halogenated or oxolated, a $C_{1-6}$ alkyloxycarbonyl, carbamoyl, carboxy, a $C_{1-6}$ alkylsulfonylamide which may be halogenated or oxolated, a $C_{1-6}$ alkylthio which may be halogenated or oxolated, a $C_{1-6}$ alkylsulfinyl which may be halogenated or oxolated, amino, hydroxy, a halogen, nitrile and 2-oxopropyl;

(9) The compound according to the above-mentioned (1), wherein $R^4$ is phenyl, thienyl or furyl, each of which may be substituted with one or more substituents selected from a group consisting of a $C_{1-6}$ alkyl which may be halogenated or oxolated, a $C_{1-6}$ alkoxy which may be halogenated or oxolated, a $C_{1-6}$ acylamino which may be halogenated or oxolated, a N—$(C_{1-6}$ alkyl)$C_{1-6}$ acylamino, a $C_{1-6}$ acyl which may be halogenated or oxolated, a $C_{1-6}$ alkylamino, a di-$C_{1-6}$ alkylamino, a $C_{1-6}$ alkenyl which may be halogenated or oxolated, a $C_{1-6}$ alkynyl which may be halogenated or oxolated, a $C_{1-6}$ alkyloxycarbonyl, carbamoyl, carboxy, a $C_{1-6}$ alkylsulfonylamide which may be halogenated or oxolated, a $C_{1-6}$ alkylthio which may be halogenated or oxolated, a $C_{1-6}$ alkylsulfinyl which may be halogenated or oxolated, amino, hydroxy, a halogen, nitrile and 2-oxopropyl;

(10) The compound according to the above-mentioned (1), wherein Z is oxygen;

(11) The compound according to the above-mentioned (1), which is 4-biphenyl-3-yl-N-pyridin-3-ylpiperazine-1-carboxamide, 4-biphenyl-3-yl-N-(3,4-dimethylisoxazol-5-yl)piperazine-1-carboxamide, N-[6-(acetylamino)pyridin-3-yl]-4-biphenyl-3-ylpiperazine-1-carboxamide, 4-(4-phenylpyridin-2-yl)-N-pyridin-3-ylpiperazine-1-carboxamide, N-(3,4-dimethylisoxazol-5-yl)-4-(4-phenylpyridin-2-yl)piperazine-1-carboxamide, 4-(4-phenylpyridin-2-yl)-N-pyridazin-3-ylpiperazine-1-carboxamide, N-(3,4-dimethylisoxazol-5-yl)-4-(5-phenylpyridin-2-yl)piperazine-1-carboxamide, 4-(5-phenylpyridin-2-yl)-N-pyridin-3-ylpiperazine-1-carboxamide, 4-biphenyl-3-yl-N-pyridazin-3-ylpiperazine-1-carboxamide, N-[4-(acetylamino)phenyl]-4-[3-(3-thienyl)phenyl]piperazine-1-carboxamide, N-(3,4-dimethylisoxazol-5-yl)-4-[3-(3-thienyl)phenyl]piperazine-1-carboxamide, N-pyridin-3-yl-4-[3-(3-thienyl)phenyl]piperazine-1-carboxamide, 4-[3-(3-furyl)phenyl]-N-pyridin-3-ylpiperazine-1-carboxamide, 4-biphenyl-4-yl-N-pyridin-3-ylpiperazine-1-carboxamide, or 4-biphenyl-4-yl-N-(3,4-dimethylisoxazol-5-yl)piperazine-1-carboxamide, or a salt thereof;

(12) A prodrug of the compound according to the above-mentioned (1) or a salt thereof;

(13) A pharmaceutical composition comprising the compound according to the above-mentioned (1) or a salt thereof or the prodrug according to the above-mentioned (12);

(14) A fatty acid amide hydrolase inhibitor comprising a compound represented by formula (I'):

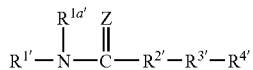

(I')

wherein Z represents an oxygen or sulfur, $R^{1'}$ represents an optionally substituted aryl or an optionally substituted heterocyclic group, $R^{1a'}$ represents a hydrogen atom, an optionally substituted hydrocarbon group, hydroxy, an optionally substituted alkoxy, an optionally substituted aryloxy, an optionally substituted amino or an optionally substituted 5- to 7-membered saturated cyclic amino, $R^{2'}$ represents an optionally substituted piperidin-1,4-diyl or an optionally substituted piperazin-1,4-diyl, $R^{3'}$ represents a divalent group formed by removing two hydrogen atoms from benzene ring which may have a further substituent or a 6-membered aromatic heterocyclic ring containing 1 to 4 heteroatoms selected from oxygen atom, sulfur atom and nitrogen atom in addition to carbon atom which may have a further substituent, and $R^{4'}$ represents a group formed by removing one hydrogen atom from an optionally substituted benzene ring or an optionally substituted 5- to 6-membered heterocyclic ring containing 1 to 4 heteroatoms selected from oxygen atom, sulfur atom and nitrogen atom in addition to carbon atom, or a salt thereof, or a prodrug thereof;

(15) A prophylactic or therapeutic agent for sleep disorder, anxiety or depression, or an analgesic agent comprising a compound represented by formula (I'):

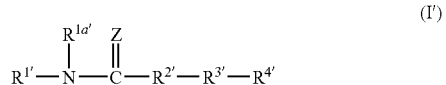

(I')

wherein Z represents an oxygen or sulfur, $R^{1'}$ represents an optionally substituted aryl or an optionally substituted heterocyclic group, $R^{1a'}$ represents a hydrogen atom, an optionally substituted hydrocarbon group, hydroxy, an optionally substituted alkoxy, an optionally substituted aryloxy, an optionally substituted amino or an optionally substituted 5- to 7-membered saturated cyclic amino, $R^{2'}$ represents an optionally substituted piperidin-1,4-diyl or an optionally substituted piperazin-1,4-diyl, $R^{3'}$ represents a divalent group formed by removing two hydrogen atoms from benzene ring which may have a further substituent or a 6-membered aromatic heterocyclic ring containing 1 to 4 heteroatoms selected from oxygen atom, sulfur atom and nitrogen atom in addition to carbon atom which may have a further substituent, and $R^{4'}$ represents a group formed by removing one hydrogen atom from an optionally substituted benzene ring or an optionally substituted 5- to 6-membered heterocyclic ring containing 1 to 4 heteroatoms selected from oxygen atom, sulfur atom and nitrogen atom in addition to carbon atom, or a salt thereof, or a prodrug thereof;

(16) Use of a compound represented by formula (I'):

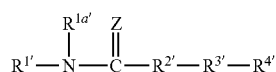

(I')

wherein Z represents an oxygen or sulfur, $R^{1'}$ represents an optionally substituted aryl or an optionally substituted heterocyclic group, $R^{1a'}$ represents a hydrogen atom, an optionally substituted hydrocarbon group, hydroxy, an optionally substituted alkoxy, an optionally substituted aryloxy, an optionally substituted amino or an optionally substituted 5- to 7-membered saturated cyclic amino, $R^{2'}$ represents an optionally substituted piperidin-1,4-diyl or an optionally substituted piperazin-1,4-diyl, $R^{3'}$ represents a divalent group formed by removing two hydrogen atoms from benzene ring which may have a further substituent or a 6-membered aromatic heterocyclic ring containing 1 to 4 heteroatoms selected from oxygen atom, sulfur atom and nitrogen atom in addition to carbon atom which may have a further substituent, and $R^{4'}$ represents a group formed by removing one hydrogen atom from an optionally substituted benzene ring or an optionally substituted 5- to 6-membered heterocyclic ring containing 1 to 4 heteroatoms selected from oxygen atom, sulfur atom and nitrogen atom in addition to carbon atom, or a salt thereof, or a prodrug thereof for manufacturing a prophylactic or therapeutic agent for sleep disorder, anxiety or depression, or an analgesic agent;

(17) A method for preventing or treating sleep disorder, anxiety or depression, or a method for pain relief, which comprises administering to a subject in need thereof an effective amount of a compound represented by formula (I'):

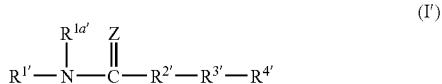

(I')

wherein Z represents an oxygen or sulfur, $R^{1'}$ represents an optionally substituted aryl or an optionally substituted heterocyclic group, $R^{1a'}$ represents a hydrogen atom, an optionally substituted hydrocarbon group, hydroxy, an optionally substituted alkoxy, an optionally substituted aryloxy, an optionally substituted amino or an optionally substituted 5- to 7-membered saturated cyclic amino, $R^{2'}$ represents an optionally substituted piperidin-1,4-diyl or an optionally substituted piperazin-1,4-diyl, $R^{3'}$ represents a divalent group formed by removing two hydrogen atoms from benzene ring which may have a further substituent or a 6-membered aromatic heterocyclic ring containing 1 to 4 heteroatoms selected from oxygen atom, sulfur atom and nitrogen atom in addition to carbon atom which may have a further substituent, and $R^{4'}$ represents a group formed by removing one hydrogen atom from an optionally substituted benzene ring or an optionally substituted 5- to 6-membered heterocyclic ring containing 1 to 4 heteroatoms selected from oxygen atom, sulfur atom and nitrogen atom in addition to carbon atom, or a salt thereof, or a prodrug thereof; and the like.

BEST MODE FOR CARRYING OUT THE INVENTION

The present invention relates to an agent for protecting a brain/neuronal cell comprising a compound having fatty acid amide hydrolase inhibitory activity. Herein, the "compound having fatty acid amide hydrolase inhibitory activity" is defined as a substance capable of directly or indirectly lowering fatty acid amide hydrolase activity. Also, the phrase "protection of brain cells and neuronal cells" means the action of inhibiting (or at least delaying) brain cells and/or neuronal cells that are subject to or may possibly be subject to cell damage, from undergoing cell death, the causes for cell damage not being particularly limited. The fatty acid amide hydrolase refers to herein an enzyme hydrolyzing a fatty acid amide (for example, N-acylated ethanolamine such as anandamide) into the corresponding fatty acid.

In the above-mentioned formula (I), $R^1$ represents an optionally substituted aryl or an optionally substituted heterocyclic group (provided that an optionally substituted quinolyl and 5-ethyl-2-methoxy-6-methyl-3-pyridinyl are excluded); $R^{1a}$ represents a hydrogen atom, an optionally substituted hydrocarbon group, hydroxy, an optionally substituted alkoxy, an optionally substituted aryloxy, an optionally substituted amino or an optionally substituted 5- to 7-membered saturated cyclic amino; $R^2$ represents an optionally substituted piperidin-1,4-diyl or an optionally substituted piperazin-1,4-diyl (provided that those substituted with propylaminomethyl, dipropylaminomethyl, cyclopropylmethylaminomethyl or dicyclopropylmethylaminomethyl are excluded); $R^3$ represents a divalent group formed by removing two hydrogen atoms from an optionally substituted 6-membered ring (preferably, a divalent group formed by removing two hydrogen atoms from an optionally substituted benzene ring or a 6-membered aromatic heterocyclic ring containing 1 to 4 heteroatoms selected from oxygen atom, sulfur atom and nitrogen atom in addition to carbon atom which may have a further substituent); and $R^4$ represents a group formed by removing one hydrogen atom from an optionally substituted benzene ring or an optionally substituted 5- to 6-membered heterocyclic ring containing 1 to 4 heteroatoms selected from oxygen atom, sulfur atom and nitrogen atom in addition to carbon atom (provided that 1-[2-(2,4-difluorophenyl)-2-hydroxy-3-(1H-1,2,4-triazol-1-yl) propyl]-5-oxo-1,5-dihydro-4H-1,2,4-triazol-4-yl and 1-[1-(4-chlorobenzoyl)propyl]-5-oxo-1,5-dihydro-4H-1,2,4-triazol-4-yl are excluded, and the substituent of the heterocyclic ring does not have phenyl group).

In the above formula (I'), $R^{1'}$ represents an optionally substituted aryl or an optionally substituted heterocyclic group, $R^{1a'}$ represents a hydrogen atom, an optionally substituted hydrocarbon group, hydroxy, an optionally substituted alkoxy, an optionally substituted aryloxy, an optionally substituted amino or an optionally substituted 5- to 7-membered saturated cyclic amino, $R^{2'}$ represents an optionally substituted piperidin-1,4-diyl or an optionally substituted piperazin-1,4-diyl, $R^{3'}$ represents a divalent group formed by removing two hydrogen atoms from benzene ring which may have a further substituent or a 6-membered aromatic heterocyclic ring containing 1 to 4 heteroatoms selected from oxygen atom, sulfur atom and nitrogen atom in addition to carbon atom which may have a further substituent, and $R^{4'}$ represents a group formed by removing one hydrogen atom from an optionally substituted benzene ring or an optionally substituted 5- to 6-membered heterocyclic ring containing 1 to 4 heteroatoms selected from oxygen atom, sulfur atom and nitrogen atom in addition to carbon atom.

As the "aryl" represented by $R^1$ or $R^{1'}$, for example, $C_{6-10}$ aryl such as phenyl, 1-naphthyl and 2-naphthyl, and the like are used.

The "aryl" may have 1 to 5, and preferably 1 to 3, substituents on substitutable positions. Herein, when the number of substituents is 2 or more, the substituents may be the same or different from each other. Examples of such substituent include a $C_{1-6}$ alkyl group which may be halogenated or oxolated (e.g., methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, isobutyl, sec-butyl, tert-butyl, 4,4,4-trifluorobutyl, pentyl, isopentyl, neopentyl, 5,5,5-trifluoropentyl, hexyl, or 6,6,6-trifluorohexyl, 2-oxopropyl, 2-oxobutyl, etc.), a $C_{1-6}$ alkoxy which may be halogenated or oxolated (e.g., methoxy, ethoxy, propoxy, isopropoxy, butoxy, isobutoxy, pentyloxy, hexyloxy, 2-oxopropoxy, 2-oxobutoxy, etc.), a $C_{1-6}$ acylamino which may be halogenated or oxolated (e.g., trifluoroacetylamino, acetoacetylamino, etc.), a N—($C_{1-6}$ alkyl)$C_{1-6}$ acylamino (e.g., N-(methyl)acetylamino, N-(methyl)propionylamino, N-(ethyl)acetylamino, etc.), a $C_{1-6}$ acyl which may be halogenated or oxolated (e.g., trifluoroacetyl, acetoacetyl, etc.), a $C_{1-6}$ alkylamino (e.g., methylamino, ethylamino, etc.), a di-$C_{1-6}$ alkylamino (e.g., dimethylamino, diethylamino, etc.), a $C_{1-6}$ alkenyl which may be halogenated or oxolated (e.g., (1E)-4,4,4-trifluoro-1-buten-1-yl, (1E)-3-oxo-1-buten-1-yl, etc.), a $C_{1-6}$ alkynyl which may be halogenated or oxolated (e.g., 4,4,4-trifluoro-1-butyn-1-yl, 3-oxo-1-butyn-1-yl, etc.), a $C_{1-6}$ alkyloxycarbonyl (e.g., methoxycarbonyl, ethoxycarbonyl, propoxycarbonyl, butoxycarbonyl, etc.), carbamoyl, carboxy, a $C_{1-6}$ alkylsulfonylamide which may be halogenated or oxolated (e.g., trifluoromethylsulfonylamino, (2-oxopropyl)sulfonylamino, etc.), a $C_{1-6}$ alkylthio which may be halogenated or oxolated (e.g., trifluoromethylthio, (2-oxopropyl)thio, etc.), a $C_{1-6}$ alkylsulfinyl which may be halogenated or oxolated (e.g., trifluoromethylsulfinyl, (2-oxopropyl)sulfinyl, etc.), amino, hydroxy, a halogen (e.g., fluorine, chlorine, bromine, iodine, etc.), nitrile, 2-oxopyrrolidin-1-yl, imidazolyl and pyrazolyl.

Examples of the "heterocyclic group" represented by $R^1$ or $R^{1'}$ include a group formed by removing one hydrogen atom from a 5- to 14-membered (preferably, 5- to 10-membered) (monocyclic to tricyclic, preferably monocyclic or bicyclic) heterocyclic ring containing 1 to 4 (preferably, 1 to 3) heteroatoms of one or two species selected from nitrogen atom, oxygen atom and sulfur atom in addition to carbon atom.

Specific examples of the "heterocyclic group" represented by $R^1$ or $R^{1'}$ include a 5-membered cyclic group containing 1 to 4 heteroatoms selected from oxygen atom, sulfur atom and nitrogen atom in addition to carbon atom such as 2- or 3-thienyl, 2- or 3-furyl, 1-, 2- or 3-pyrrolyl, 1-, 2- or 3-pyrrolidinyl, 2-, 4- or 5-oxazolyl, 3-, 4- or 5-isoxazolyl, 2-, 4- or 5-thiazolyl, 3-, 4- or 5-isothiazolyl, 3-, 4- or 5-pyrazolyl, 2-, 3- or 4-pyrazolidinyl, 2-, 4- or 5-imidazolyl, 1,2,3-triazolyl, 1,2,4-triazolyl, and 1H- or 2H-tetrazolyl; a 6-membered cyclic group containing 1 to 4 heteroatoms selected from oxygen atom, sulfur atom and nitrogen atom in addition to carbon atom such as 2-, 3- or 4-pyridyl, N-oxido-2-, 3- or 4-pyridyl, 2-, 4- or 5-pyrimidinyl, N-oxido-2-, 4- or 5-pyrimidinyl, thiomorpholinyl, morpholinyl, piperidino, 2-, 3- or 4-piperidyl, thiopyranyl, 1,4-oxadinyl, 1,4-thiadinyl, 1,3-thiadinyl, piperazinyl, triazinyl, 3- or 4-pyridazinyl, pyrazinyl, and N-oxido-3- or 4-pyridazinyl; a bicyclic or tricyclic fused-ring group containing 1 to 4 heteroatoms selected from oxygen atom, sulfur atom and nitrogen atom in addition to carbon atom (preferably, a group formed by condensing the above-mentioned 5- to 6-membered ring with one or two 5- to 6-membered cyclic groups optionally containing 1 to 4 heteroatoms selected from oxygen atom, sulfur atom and nitrogen atom in addition to carbon atom) such as indolyl, benzofuryl, benzothiazolyl, benzisoxazolyl, benzoxazolyl, benzimidazolyl, indazolyl, isoxazolopyridyl, benzoxinyl, benzotriazolyl, benzodioxolyl, quinolyl, isoquinolyl, phthalazinyl, quinazolinyl, quinoxalinyl, indolizinyl, quinolizinyl, 1,8-naphthylidinyl, dibenzofuranyl, carbazolyl, acridinyl, phenanthridinyl, chromanyl, phenothiazinyl, phenoxazinyl, dihydrobenzofuryl, imidazopyridinyl, imidazopyridazinyl, etc.; and the like. Among these, a bicyclic heterocyclic group in which a 5- to 7-membered (preferably, 5- or 6-membered) heterocyclic ring containing 1 to 3 heteroatoms selected from oxygen atom, sulfur atom and nitrogen atom in addition to carbon atom is condensed with a benzene ring is preferred.

The "heterocyclic group" may have 1 to 5, preferably 1 to 3 substituents on substitutable positions. Herein, when the number of substituents is two or more, the substituents may be the same or different from each other. Examples of such substituent are exemplified by those for the above-mentioned substituent of "aryl".

Examples of the "hydrocarbon group" represented by $R^{1a}$ and $R^{1a'}$ include an aliphatic hydrocarbon group, a monocyclic saturated hydrocarbon group and an aromatic hydrocarbon group, and an aliphatic hydrocarbon group having 1 to 6 carbon atoms is preferred. Specifically, for example, an alkyl group, an alkenyl group, an alkynyl group, and the like are used.

The "alkyl group" is preferably, for example, a lower alkyl group and the like, and for example, a $C_{1-6}$ alkyl group such as methyl, ethyl, propyl, isopropyl, butyl, isobutyl, sec-butyl and tert-butyl, pentyl, hexyl, and the like are used.

The "alkenyl group" is preferably, for example, a lower alkenyl group and the like, and for example, a $C_{2-6}$ alkenyl group such as vinyl, 1-propenyl, allyl, isopropenyl, butenyl, isobutenyl, and the like are used.

The "alkynyl group" is preferably, for example, a lower alkynyl group and the like, and for example, a $C_{2-6}$ alkynyl group such as ethynyl, propargyl, 1-propynyl, and the like are used.

The "hydrocarbon group" may have 1 to 5, preferably 1 to 3 substituents on substitutable positions. Herein, when the number of substituents is 2 or more, the substituents may be the same or different from each other. Examples of such substituent include a hydroxy, a carbamoyl, a lower alkyl (e.g., a $C_{1-6}$ alkyl group such as methyl, ethyl, propyl, isopropyl, butyl, isobutyl, sec-butyl, tert-butyl, pentyl, isopentyl, neopentyl, hexyl, etc.), a lower alkoxy (e.g., a $C_{1-6}$ alkoxy group such as methoxy, ethoxy, propoxy, isopropoxy, butoxy, isobutoxy, pentyloxy, hexyloxy, etc.), a halogen atom (e.g., fluorine, chlorine, bromine, iodine, etc.), and the like.

Examples of the "alkoxy" of the "optionally substituted alkoxy" represented by $R^{1a}$ and $R^{1a'}$ include $C_{1-6}$ alkoxy such as methoxy, ethoxy, propoxy, isopropoxy, butoxy, isobutoxy, sec-butoxy or tert-butoxy, and examples of the substituent which may be possessed by the "alkoxy" include the same substituents as those which may be possessed by the "hydrocarbon group" of the above-mentioned "optionally substituted hydrocarbon group".

Examples of the "aryloxy" of the "optionally substituted aryloxy" represented by $R^{1a}$ and $R^{1a'}$ include $C_{6-14}$ aryloxy such as phenyloxy and naphthyloxy, and examples of the substituent which may be possessed by the "aryloxy" include the same substituents as those which may be possessed by the above-mentioned "optionally substituted hydrocarbon group".

Examples of the "optionally substituted amino" represented by $R^{1a}$ and $R^{1a'}$ include amino, mono-$C_{1-6}$ alkylamino (e.g., methylamino, ethylamino, etc.), mono-$C_{6-14}$ arylamino (e.g., phenylamino, 1-naphthylamino, 2-naphthylamino, etc.), di-$C_{1-6}$ alkylamino (e.g., dimethylamino, diethylamino, etc.), di-$C_{6-14}$ arylamino (e.g., diphenylamino, etc.) and acylamino.

Examples of the acylamino include $C_{1-6}$ alkyl-carbonylamino such as acetylamino, propionylamino, butyrylamino or isobutyrylamino, and examples of the substituent which may be possessed by the "amino" include the same substituents as those which may be possessed by the above-mentioned "optionally substituted hydrocarbon group".

Examples of the "5- to 7-membered saturated cyclic amino" of the "optionally substituted 5- to 7-membered saturated cyclic amino" represented by $R^{1a}$ and $R^{1a'}$ include a 5- to 7-membered cyclic amino group which may contain 1 to 3 heteroatoms selected from oxygen atom, sulfur atom and nitrogen atom in addition to carbon atoms and one nitrogen atom. Specific examples thereof include a 5- to 7-membered cyclic amino group such as pyrrolidinyl, pyrazolidinyl, imidazolidinyl, thiazolidinyl, oxazolidinyl, piperidyl, morpholinyl, thiomorpholinyl, piperazinyl and azepinyl.

Examples of the substituent which may be possessed by the "5- to 7-membered saturated cyclic amino" include the same substituents as those which may be possessed by the "hydrocarbon group" of the above-mentioned "optionally substituted hydrocarbon group".

Examples of the substituent which may be possessed by the "optionally substituted piperidin-1,4-diyl" or "optionally substituted piperazin-1,4-diyl" represented by $R^2$ or $R^{2'}$ include a $C_{1-6}$ alkyl which may be halogenated or oxolated (e.g., methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, isobutyl, sec-butyl, tert-butyl, 4,4,4-trifluorobutyl, pentyl, isopentyl, neopentyl, 5,5,5-trifluoropentyl, hexyl, 6,6,6-trifluorohexyl, 2-oxopropyl, 2-oxobutyl, etc.), a $C_{1-6}$ alkoxy which may be halogenated or oxolated (e.g., methoxy, ethoxy, propoxy, isopropoxy, butoxy, isobutoxy, pentyloxy, hexyloxy, 2-oxopropoxy, 2-oxobutoxy, etc.), a $C_{1-6}$ acylamino which may be halogenated or oxolated (e.g., trifluoroacetylamino, acetoacetylamino, etc.), a N—($C_{1-6}$ alkyl) $C_{1-6}$ acylamino (e.g., N-(methyl)acetylamino, N-(methyl)propionylamino, N-(ethyl)acetylamino, etc.), a $C_{1-6}$ acyl which may be halogenated or oxolated (e.g., trifluoroacetyl, acetoacetyl, etc.), a $C_{1-6}$ alkylamino (e.g., methylamino, ethylamino, etc.), a di-$C_{1-6}$ alkylamino (e.g., dimethylamino, diethylamino, etc.), a $C_{1-6}$ alkenyl which may be halogenated or oxolated (e.g., (1E)-4,4,4-trifluoro-1-buten-1-yl, (1E)-3-oxo-1-buten-1-yl, etc.), a $C_{1-6}$ alkynyl which may be halogenated or oxolated (e.g., 4,4,4-trifluoro-1-butyn-1-yl, 3-oxo-1-butyn-1-yl, etc.), a $C_{1-6}$ alkyloxycarbonyl (e.g., methoxycarbonyl, ethoxycarbonyl, propoxycarbonyl, butoxycarbonyl, etc.), carbamoyl, carboxy, a $C_{1-6}$ alkylsulfonylamino which may be halogenated or oxolated (e.g., trifluoromethylsulfonylamino, (2-oxopropyl)sulfonylamino, etc.), a $C_{1-6}$ alkylthio which may be halogenated or oxolated (e.g., trifluoromethylthio, (2-oxopropyl)thio, etc.), a $C_{1-6}$ alkylsulfinyl which may be halogenated or oxolated (e.g., trifluoromethylsulfinyl, (2-oxopropyl)sulfinyl, etc.), amino, hydroxy, a halogen (e.g., fluorine, chlorine, bromine, iodine, etc.), nitrile and the like. $R^2$ or $R^{2'}$ may have 1 or more substituents on substitutable positions, and when there are plural substituents, they may be the same or different. In addition, when $R^2$ or $R^{2'}$ is "optionally substituted piperidin-1,4-diyl", its direction may be in any direction, as shown in the following formulas:

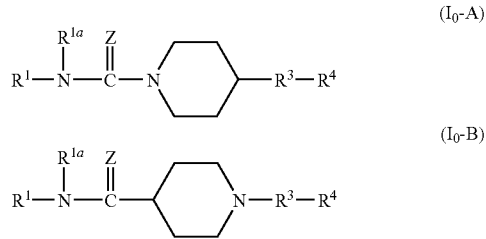

and the direction as indicated in the formula ($I_0$-A) is preferred.

That is, the moiety represented by the formula: —C(=Z)—$R^2$— is preferably a moiety represented by formula:

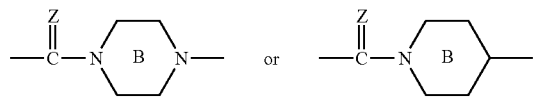

wherein ring B represents piperidine or piperazine which may be substituted with one or more substituents selected from a group consisting of an optionally halogenated or oxolated $C_{1-6}$ alkyl, an optionally halogenated or oxolated $C_{1-6}$ alkoxy, an optionally halogenated or oxolated $C_{1-6}$ acylamino, a N—($C_{1-6}$ alkyl)$C_{1-6}$ acylamino, an optionally halogenated or oxolated $C_{1-6}$ acyl, a $C_{1-6}$ alkylamino, a di$C_{1-6}$ alkylamino, an optionally halogenated or oxolated $C_{1-6}$ alkenyl, an optionally halogenated or oxolated $C_{1-6}$ alkynyl, a $C_{1-6}$ alkyloxycarbonyl, carbamoyl, carboxy, an optionally halogenated or oxolated $C_{1-6}$ alkylsulfonylamido, an optionally halogenated or oxolated $C_{1-6}$ alkylthio, an optionally halogenated or oxolated $C_{1-6}$ alkylsulfinyl, amino, hydroxy, halogen, nitrile, 2-oxopyrrolidin-1-yl and 2-oxopropyl.

Examples of the substituent in the "divalent group formed by removing two hydrogen atoms from benzene ring which may have a further substituent" represented by $R^3$ or $R^{3'}$ include a $C_{1-6}$ alkyl which may be halogenated or oxolated (e.g., methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, isobutyl, sec-butyl, tert-butyl, 4,4,4-trifluorobutyl, pentyl, isopentyl, neopentyl, 5,5,5-trifluoropentyl, hexyl, 6,6,6-trifluorohexyl, 2-oxopropyl, 2-oxobutyl, etc.), a $C_{1-6}$ alkoxy which may be halogenated or oxolated (e.g., methoxy, ethoxy, propoxy, isopropoxy, butoxy, isobutoxy, pentyloxy, hexyloxy, 2-oxopropoxy, 2-oxobutoxy, etc.), a $C_{1-6}$ acylamino which may be halogenated or oxolated (e.g., trifluoroacetylamino, acetoacetylamino, etc.), a N—($C_{1-6}$ alkyl) $C_{1-6}$ acylamino (e.g., N-(methyl)acetylamino, N-(methyl)propionylamino, N-(ethyl)acetylamino, etc.), a $C_{1-6}$ acyl which may be halogenated or oxolated (e.g., trifluoroacetyl, acetoacetyl, etc.), a $C_{1-6}$ alkylamino (e.g., methylamino, ethylamino, etc.), a di-$C_{1-6}$ alkylamino (e.g., dimethylamino, diethylamino, etc.), a $C_{1-6}$ alkenyl which may be halogenated or oxolated (e.g., (1E)-4,4,4-trifluoro-1-buten-1-yl, (1E)-3-oxo-1-buten-1-yl, etc.), a $C_{1-6}$ alkynyl which may be halogenated or oxolated (e.g., 4,4,4-trifluoro-1-butyn-1-yl, 3-oxo-1-butyn-1-yl, etc.), a $C_{1-6}$ alkyloxycarbonyl (e.g., methoxycarbonyl, ethoxycarbonyl, propoxycarbonyl, butoxycarbonyl, etc.), carbamoyl, carboxy, a $C_{1-6}$ alkylsulfonylamino which may be halogenated or oxolated (e.g., trifluoromethylsulfonylamino, (2-oxopropyl)sulfonylamino, etc.), a $C_{1-6}$ alkylthio which may be halogenated or oxolated (e.g., trifluoromethylthio, (2-oxopropyl)thio, etc.), a $C_{1-6}$ alkylsulfinyl which may be halogenated or oxolated (e.g., trifluoromethylsulfinyl, (2-oxopropyl)sulfinyl, etc.), amino, hydroxy, a halogen (e.g., fluorine, chlorine, bromine, iodine, etc.), nitrile and the like.

Examples of the "group formed by removing two hydrogen atoms from 6-membered aromatic heterocyclic ring containing 1 to 4 heteroatoms selected from oxygen atom, sulfur atom and nitrogen atom" of the "group formed by removing two hydrogen atoms from 6-membered aromatic heterocyclic ring containing 1 to 4 heteroatoms selected from oxygen atom, sulfur atom and nitrogen atom which may have a further substituent" represented by $R^3$ or $R^{3'}$ include a group formed by removing two hydrogen atoms from a 6-membered aromatic heterocyclic ring such as pyridine, pyrimidine, pyrazine, triazine, oxazine and thiazine. Specifically, pyridin-2,4-diyl and the like are preferably used.

In addition, examples of the substituent of these "group formed by removing two hydrogen atoms from 6-membered aromatic heterocyclic ring containing 1 to 4 heteroatoms selected from oxygen atom, sulfur atom and nitrogen atom" include the same substituents as those exemplified with respect to the substituents for the above-mentioned "divalent group formed by removing two hydrogen atoms from benzene ring", and one or more substituents may be possessed on substitutable positions. When there are plural substituents, they may be the same or different.

As $R^3$ or $R^{3'}$, a group optionally having a substituent represented by formula;

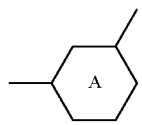

wherein, ring A represents benzene ring or 6-membered aromatic heterocyclic ring, in particular, 1,3-phenylene group is preferred.

Examples of the substituent in the "group formed by removing one hydrogen atom from an optionally substituted benzene ring" represented by $R^4$ or $R^{4'}$ include the same substituents as those exemplified with respect to the substituents for the "divalent group formed by removing two hydrogen atoms from benzene ring which may have a further substituent" represented by $R^3$ or $R^{3'}$, and the benzene ring may have one or more substituents on substitutable positions. When plural substituents are possessed, they may be the same or different.

Examples of the "5- to 6-membered heterocyclic ring" of the "group formed by removing one hydrogen atom from an optionally substituted 5- to 6-membered heterocyclic ring containing 1 to 4 heteroatoms selected from oxygen atom, sulfur atom and nitrogen atom in addition to carbon atom" represented by $R^4$ or $R^{4'}$ include the same heterocyclic ring as those exemplified with respect to the heterocyclic ring in the 5- to 6-membered heterocyclic group of the above-mentioned "optionally substituted heterocyclic group" represented by $R^1$. Specific examples of such heterocyclic ring include a monocyclic aromatic heterocyclic ring such as furan, thiophene, pyrazole, thiazole, oxazole, 1,2,4-oxadiazole, 1,3,4-oxadiazole, isothiazole, 1,2,4-thiadiazole, 1,3,4-thiadiazole, isoxazole, tetrazol, pyridine, pyrazine, pyrimidine, pyridazine and triazole; a monocyclic non-aromatic heterocyclic ring such as tetrahydrofuran, tetrahydrothiophene, dithiolan, oxathiolane, pyrrolidine, pyrroline, imidazolidine, imidazoline, pyrazolidine, pyrazoline, piperidine, piperazine, oxazine, oxadiazine, thiazine, thiadiazine, morpholine, thiomorpholine, pyran, tetrahydropyran, tetrahydrothiopyran; and a fused aromatic heterocyclic ring such as benzothiophene, benzofuran, benzimidazole, benzoxazole, benzothiazole, benzisothiazole, naphtho[2,3-b]thiophene, phenoxathiin, indole, isoindole, 1H-indazole, purine, 4H-quinolizine, isoquinoline, quinoline, phthalazine, naphthyridine, quinoxaline, quinazoline, cinnoline, carbazole, β-carboline, phenanthridine, acridine, phenazine, phenothiazine, furazan, phenoxazine and phthalimide. In addition, heterocyclic rings wherein some or all unsaturated bonds in these aromatic heterocyclic rings are changed to saturated bond may be used. Furthermore, examples of their substituent include the same substituents as those exemplified with respect to the substituents which the above-mentioned "group formed by removing one hydrogen atom from an optionally substituted benzene ring" may have. The "heterocyclic ring" may have one or more substituents at substitutable positions, and when there are plural substituents, they may be the same or different.

Phenyl is particularly preferred as $R^4$ or $R^{4'}$.

As the compound represented by formula (I), preferred is a compound wherein $R^1$ is phenyl, benzisoxazolyl, isoxazolyl, pyridyl, pyridazinyl, pyrazinyl, pyrimidinyl or pyrazolyl, each of which may be substituted with one or more substituents selected from a group consisting of a $C_{1-6}$ alkyl which may be halogenated or oxolated, a $C_{1-6}$ alkoxy which may be halogenated or oxolated, a $C_{1-6}$ acylamino which may be halogenated or oxolated, a N—($C_{1-6}$ alkyl)$C_{1-6}$ acylamino, a $C_{1-6}$ acyl which may be halogenated or oxolated, a $C_{1-6}$ alkylamino, a di-$C_{1-6}$ alkylamino, a $C_{1-6}$ alkenyl which may be halogenated or oxolated, a $C_{1-6}$ alkynyl which may be halogenated or oxolated, a $C_{1-6}$ alkyloxycarbonyl, carbamoyl, carboxy, a $C_{1-6}$ alkylsulfonylamide which may be halogenated or oxolated, a $C_{1-6}$ alkylthio which may be halogenated or oxolated, a $C_{1-6}$ alkylsulfinyl which may be halogenated or oxolated, amino, hydroxy, a halogen, nitrile, 2-oxopyrrolidin-1-yl, 2-oxopropyl, imidazolyl and pyrazolyl, $R^{1a}$ is hydrogen, the moiety represented by formula: —C(=Z)—$R^2$— is a divalent group represented by formula:

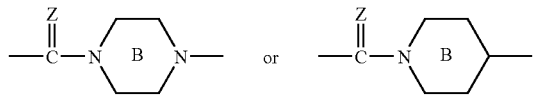

wherein ring B represents piperidine or piperazine, each of which may be substituted with one or more substituents selected from a group consisting of a $C_{1-6}$ alkyl which may be halogenated or oxolated, a $C_{1-6}$ alkoxy which may be halogenated or oxolated, a $C_{1-6}$ acylamino which may be halogenated or oxolated, a N—($C_{1-6}$ alkyl)$C_{1-6}$ acylamino, a $C_{1-6}$ acyl which may be halogenated or oxolated, a $C_{1-6}$ alkylamino, a di-$C_{1-6}$ alkylamino, a $C_{1-6}$ alkenyl which may be halogenated or oxolated, a $C_{1-6}$ alkynyl which may be halogenated or oxolated, a $C_{1-6}$ alkyloxycarbonyl, carbamoyl, carboxy, a $C_{1-6}$ alkylsulfonylamide which may be halogenated or oxolated, a $C_{1-6}$ alkylthio which may be halogenated or oxolated, a $C_{1-6}$ alkylsulfinyl which may be halogenated or oxolated, amino, hydroxy, a halogen, nitrile, 2-oxopyrrolidin-1-yl and 2-oxopropyl, $R^3$ is a divalent group represented by formula:

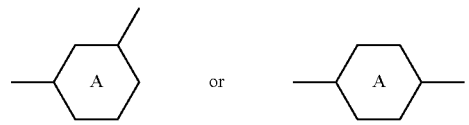

wherein ring A represents benzene ring or a 6-membered aromatic heterocyclic ring, which may have one or more substituents selected from a group consisting of a $C_{1-6}$ alkyl which may be halogenated or oxolated, a $C_{1-6}$ alkoxy which may be halogenated or oxolated, a $C_{1-6}$ acylamino which may be halogenated or oxolated, a N—($C_{1-6}$ alkyl)$C_{1-6}$ acylamino, a $C_{1-6}$ acyl which may be halogenated or oxolated, a $C_{1-6}$ alkylamino, a di-$C_{1-6}$ alkylamino, a $C_{1-6}$ alkenyl which may be halogenated or oxolated, a $C_{1-6}$ alkynyl which may be halogenated or oxolated, a $C_{1-6}$ alkyloxycarbonyl, carbamoyl, carboxy, a $C_{1-6}$ alkylsulfonylamide which may be halogenated or oxolated, a $C_{1-6}$ alkylthio which may be halogenated or oxolated, a $C_{1-6}$ alkylsulfinyl which may be halogenated or oxolated, amino, hydroxy, a halogen, nitrile and 2-oxopropyl (preferably, 1,3-phenylene, 1,4-phenylene, pyridyl-2,4-diyl or pyridyl-2,5-diyl, each of which may have one or more substituents selected from a group consisting of a $C_{1-6}$ alkyl which may be halogenated or oxolated, a $C_{1-6}$ alkoxy which may be halogenated or oxolated, a $C_{1-6}$ acylamino which may be halogenated or oxolated, a N—($C_{1-6}$ alkyl)$C_{1-6}$ acylamino, a $C_{1-6}$ acyl which may be halogenated or oxolated, a $C_{1-6}$ alkylamino, a di-$C_{1-6}$ alkylamino, a $C_{1-6}$ alkenyl which may be halogenated or oxolated, a $C_{1-6}$ alkynyl which may be halogenated or oxolated, a $C_{1-6}$ alkyloxycarbonyl, carbamoyl, carboxy, a $C_{1-6}$ alkylsulfonylamide which may be halogenated or oxolated, a $C_{1-6}$ alkylthio which may be halogenated or oxolated, a $C_{1-6}$ alkylsulfinyl which may be halogenated or oxolated, amino, hydroxy, a halogen, nitrile and 2-oxopropyl), $R^4$ is phenyl, thienyl (e.g., 2-thienyl, 3-thienyl) or furyl (2-furyl, 3-furyl), each of which may be substituted with one or more substituents selected from a group consisting of a $C_{1-6}$ alkyl which may be halogenated or oxolated, a $C_{1-6}$ alkoxy which may be halogenated or oxolated, a $C_{1-6}$ acylamino which may be halogenated or oxolated, a N—($C_{1-6}$ alkyl)$C_{1-6}$ acylamino, a $C_{1-6}$ acyl which may be halogenated or oxolated, a $C_{1-6}$ alkylamino, a di-$C_{1-6}$ alkylamino, a $C_{1-6}$ alkenyl which may be halogenated or oxolated, a $C_{1-6}$ alkynyl which may be halogenated or oxolated, a $C_{1-6}$ alkyloxycarbonyl, carbamoyl, carboxy, a $C_{1-6}$ alkylsulfonylamide which may be halogenated or oxolated, a $C_{1-6}$ alkylthio which may be halogenated or oxolated, a $C_{1-6}$ alkylsulfinyl which may be halogenated or oxolated, amino, hydroxy, a halogen, nitrile and 2-oxopropyl, and Z is oxygen.

Examples of the salt of the compound represented by the formula (I) or (I') include metal salts, ammonium salts, salts with organic bases, salts with inorganic acids, salts with organic acids, salts with basic or acidic amino acids, and the like. Suitable examples of the metal salt include alkali metal salts such as sodium salts and potassium salts; alkaline earth metal salts such as calcium salts, magnesium salts and barium salts; aluminum salts; and the like. Suitable examples of the salt with organic base include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Suitable examples of the salt with inorganic acid include salts with hydrochloric acid, hydrobromic acid, nitric acid, sulfuric acid, phosphoric acid and the like. Suitable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Suitable examples of the salt with basic amino acid include salts with arginine, lysine, ornithine and the like, and suitable examples of the salt with acidic amino acid include salts with aspartic acid, glutamic acid and the like.

Among these, pharmaceutically acceptable salts are preferred. For example, in case that the compound has an acidic functional group, inorganic salts such as alkali metal salts (e.g., sodium salts, potassium salts, etc.) and alkaline earth metal salts (e.g., calcium salts, magnesium salts, barium salts, etc.), ammonium salts, and the like may be used, while in case that the compound has a basic functional group, salts with inorganic acids such as hydrochloric acid, hydrobromic acid, nitric acid, sulfuric acid and phosphoric acid, and salts with organic acids such as acetic acid, phthalic acid, fumaric acid, oxalic acid, tartaric acid, maleic acid, citric acid, succinic acid, methanesulfonic acid, p-toluenesulfonic acid and the like, may be used.

A prodrug of compound (I) or (I') refers to a compound that is converted into compound (I) or (I') by a reaction with enzyme, gastric acid or the like under a physiological condition in the living body, that is, a compound that is converted into compound (I) or (I') by an enzymatic oxidation, reduction, hydrolysis or the like, or a compound that is converted into compound (I) or (I') of the present invention by hydrolysis with gastric acid or the like.

Examples of the prodrug of compound (I) or (I') include a compound in which an amino group of compound (I) or (I') is acylated, alkylated or phosphorylated (e.g., a compound in which an amino group of compound (I) or (I') of the invention is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated, tert-butylated or the like); a compound in which a hydroxyl group of compound (I) or (I') is acylated, alkylated, phosphorylated or converted into borate (e.g., a compound in which a hydroxyl group of compound (I) or (I') is acetylated, palmitoylated, propanoylated, pivaloylated, succinylated, fumarylated, alanylated, dimethylaminomethylcarbonylated or the like); a compound in which a carboxyl group of compound (I) or (I') is esterified or amidated (e.g., a compound in which a carboxyl group of compound (I) or (I') is ethyl esterified, phenyl esterified, carboxymethyl esterified, dimethylaminomethyl esterified, pivaloyloxymethyl esterified, ethoxycarbonyloxyethyl esterified, phthalidyl esterified, (5-methyl-2-oxo-1,3-dioxolen-4-yl)methyl esterified, cyclohexyloxycarbonylethyl esterified, methylamidated or the like); and the like. These compounds can be prepared from compound (I) or (I') of the present invention by a method known per se.

In addition, the prodrug of compound (I) or (I') may be a compound which is converted into compound (I) or (I') of the present invention under physiological conditions as described in "Development of Drugs", Vol. 7, Molecular Design, Hirokawa Shoten, pages 163-198 (1990).

When compound (I) or (I') has isomers such as optical isomers, stereoisomers, regioisomers or rotational isomers, compound (I) or (I') encompasses individual isomers and a mixture thereof. For example, when optical isomers of compound (I) or (I') are present, the optical isomers obtained by resolution of racemates are also included in compound (I) or (I'). These isomers each can be obtained as a single product by synthetic means known per se or separation means (concentration, solvent extraction, column chromatography, recrystallization, etc.).

Compound (I) or (I') may be in the form of crystals, and compound (I) or (I') encompasses both single crystalline forms and mixed crystalline forms. Crystals can be prepared by crystallization according to crystallization methods known per se.

Compound (I) or (I') may be either a solvate (e.g., hydrate, etc.) or a non-solvate, and both of them are encompassed in compound (I) or (I').

Compound (I) or (I') also encompasses compounds labeled with isotopes (e.g., $^3H$, $^{14}C$, $^{35}S$, $^{125}I$, etc.).

Hereinafter, a process for preparation of compound (I) or (I') will be illustrated. Although compound (I) wherein $R^2$ is piperazin-1,4-diyl will be specifically explained herein, other compounds can be also easily prepared according to this process. In addition, when $R^3$ is a divalent group wherein some or all unsaturated bonds of benzene ring or 6-membered aromatic heterocyclic ring are saturated, they can be produced by the following method or an analogous method thereto.

[Preparation Process 1]

Compound (I) of the present invention can be prepared, for example, according to Preparation Process 1 represented by the following scheme:

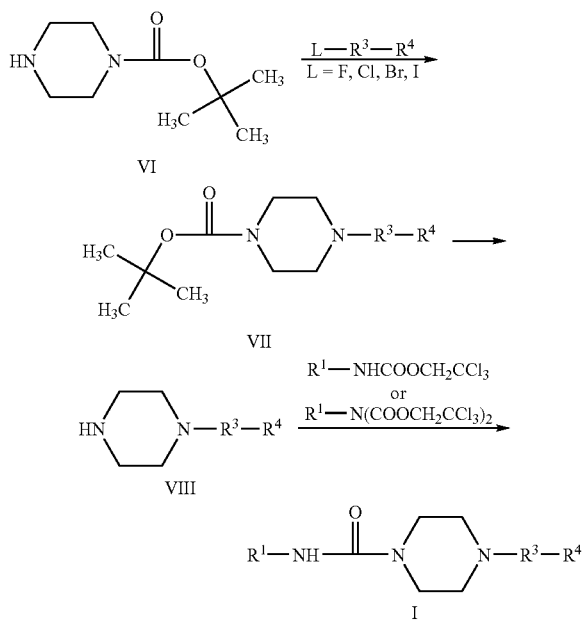

wherein each symbol is as defined above, or an analogous method thereto.

According to Preparation Process 1, first, compound (VI) is subjected to a substitution reaction to prepare compound (VII).

The substitution reaction is carried out according to a conventional method in the presence of a base and halide in a solvent having no adverse effect on the reaction. Examples of the base include potassium carbonate, sodium carbonate, sodium hydride, potassium hydride and the like.

Examples of the halide include chloride, bromide, iodide, and the like.

The amounts of the base and halide to be used are preferably about 1 to about 5 molar equivalents, respectively, relative to Compound (VI).

Examples of the solvent having no adverse effect on the reaction include ethers such as tetrahydrofuran; halogenated hydrocarbons such as chloroform; aromatic hydrocarbons such as N,N-dimethylformamide; sulfoxides such as dimethylsulfoxide; and the like. These solvents may be used by mixing two or more at an appropriate ratio. The amount of these solvents to be used is, for example, 1 to 100 fold-volumes relative to compound (VI).

The reaction temperature is usually about −50° C. to about 250° C., preferably 0° C. to 120° C.

The reaction time is usually about 0.5 to about 36 hours. The thus obtained compound (VII) can be isolated and purified by known separation and purification means such as concentration, concentration under reduced pressure, extraction with solvent, crystallization, recrystallization, transfer dissolution and chromatography. Further, compound (VII) may be used in the subsequent reaction without being isolated.

Next, Compound (VIII) is prepared by removing tert-butoxycarbonyl group of compound (VII).

This reaction is carried out by reacting an acid in a solvent having no adverse effect on the reaction according to a conventional method.

Examples of the acid include hydrochloric acid, hydrobromic acid, sulfuric acid, trifluoroacetic acid, trifluoromethanesulfonic acid and the like. The amount of the acid to be used is preferably about 1 to about 100 molar equivalents relative to compound (VII).

Examples of the solvent having no adverse effect on the reaction include alcohols such as methanol; ethers such as tetrahydrofuran; halogenated hydrocarbons such as chloroform; aromatic hydrocarbons such as toluene; amides such as N,N-dimethylformamide; sulfoxides such as dimethylsulfoxide; and the like. These solvents may be used by mixing two or more at an appropriate ratio. The amount of these solvents to be used is, for example, 1 to 100 fold-volumes relative to compound (VII).

The reaction temperature is usually about −50° C. to about 250° C., preferably 0° C. to 120° C.

The reaction time is usually about 0.5 to about 24 hours.

The thus obtained compound (VIII) can be isolated and purified by known separation and purification means such as concentration, concentration under reduced pressure, extraction with solvent, crystallization, recrystallization, transfer dissolution and chromatography. Further, compound (VIII) may be used in the subsequent reaction without being isolated.

Next, compound (VIII) is subjected to an ureidation reaction to prepare compound (I).

This reaction is carried out according to a conventional method, in the presence of a base and 2,2,2-trichloroethoxycarbamate in a solvent having no adverse effect on the reaction. Examples of the base include pyridine, triethylamine, diisopropylethylamine, potassium carbonate, sodium carbonate, sodium hydride, potassium hydride and the like.

Examples of the solvent having no adverse effect on the reaction include ethers such as tetrahydrofuran; halogenated hydrocarbons such as chloroform; aromatic hydrocarbons such as toluene; amides such as N,N-dimethylformamide; sulfoxides such as dimethylsulfoxide; and the like. These solvents may be used by mixing two or more at an appropriate ratio. The amount of these solvents to be used is, for example, 1 to 100 fold-volumes relative to compound (VIII).

The reaction temperature is usually about −50° C. to 200° C.

The reaction time is usually about 0.5 to about 36 hours.

The thus obtained compound (I) can be isolated and purified by known separation and purification means such as concentration, concentration under reduced pressure, extraction with solvent, crystallization, recrystallization, transfer dissolution and chromatography.

As described in Examples hereinafter, administration of a compound having FAAH inhibitory activity markedly reduces infarct volume in a cerebral ischemic model, and this implies that a compound having FAAH inhibitory activity has a brain/neuronal cell protective effect, in particular, a brain/neuronal cell protective effect against cerebrovascular disorders, head injury or spinal cord damage. Therefore, the compound having FAAH inhibitory activity is useful for a prevention and treatment of diseases in which protection of brain cells and neuronal cells from cell damage is effective prophylactically and therapeutically, preferably cerebrovascular disorders (e.g., cerebral infarction, cerebral hemorrhage, subarachnoid hemorrhage, etc.), head injury and spinal cord damage. Further, examples of the diseases that are believed to be benefited by the compound of the present invention in prevention and treatment thereof include, but not limited to, diseases similarly caused by disorders of brain cells and neuronal cells, such as brain disorders upon resuscitation after cardiac arrest, decrease in brain function before and after brain surgery, hypoxia, hypoglycemia, brain or spinal cord trauma, drug intoxication, gas poisoning, diabetes mellitus, administration of antitumor agent, nervous system disorders due to alcohol or the like, senile dementia such as Alzheimer's disease, Parkinson's disease, Huntington's chorea, prion disease, amyotrophic lateral sclerosis, spinocerebellar degeneration, anxiety, depression, sleep disorders, eating disorders, obesity, frequent urination, urinary incontinence, interstitial cystitis, Crohn's disease, colonitis, colitis, colon cancer, large intestine cancer, contraception and AIDS. Such compound having FAAH inhibitory activity is particularly preferably a piperazine compound and compound (I') or a salt or prodrug thereof (hereinafter, referred to as the compound of the present invention in some cases).

Meanwhile, since compound (I') of the present invention has FAAH inhibitory activity, it is useful, based on the above-described knowledge in the art, as a prophylactic and/or therapeutic agent for nausea, sicchasia or vomiting caused by anticancer agent; cancer- or infection (e.g., AIDS, etc.)-associated apocleisis or cachectic anorexia; convulsion, pain, tremor, nystagmus or enuresis due to multiple sclerosis; neuropathic pain; chronic pain; Huntington's chorea; Tourette's syndrome; dyskinesia initiated by levodopa; locomotor disorder; asthma; glaucoma; allergy; inflammation; epilepsy; autoimmune diseases; diarrhea; obesity; sleep disorder; depression; anxiety; mental diseases; Crohn's disease; Alzheimer's disease; interstitial cystitis; AIDS; colonitis; colitis; colon cancer; rectal cancer; hypertriglyceridemia; hyperlipidemia; diabetes mellitus; arteriosclerosis; or Parkinson's disease, or as a contraceptive or analgesic.

Furthermore, since FAAH is an enzyme which hydrolyzes an endogenous sleep substance, oleamide, a FAAH inhibitory agent induces sleep by suppressing the decomposition of oleamide. Therefore, the compound ($I_O$) and the like of the present invention is useful as a prophylactic and/or therapeutic agent of sleep abnormality such as sleep disorders, for example, intrinsic sleep disorders (e.g., psychophysiological insomnia), extrinsic sleep disorders, circadian rhythm disorders (e.g., time zone change (jet lag) syndrome, shift work sleep disorder, irregular sleep-wake pattern, delayed sleep phase syndrome, advanced sleep phase syndrome, non-24 hour sleep-wake), and the like; parasomunias; and sleep disorders associated with medical or neurological disorders (e.g., chronic obstructive pulmonary disease, Alzheimer's disease, Parkinson's disease, cerebrovascular dementia, schizophrenia, depression, anxiety neurosis).

The FAAH inhibitory activity of a compound can be conveniently and simply measured by a method for measuring fatty acid amide hydrolase activity or fatty acid amide hydrolase inhibitory activity, which has been newly developed by the present inventors. The present inventors have unexpectedly found that a resin having a polar group which is generally used in adsorption of proteins or nucleic acids, can also adsorb fatty acid amides of medium- to long-chained fatty acids having 8 or more carbon atoms, thus completing the method of the present invention. This method is characterized by adsorption of a fatty acid amide onto a resin having a polar group.

One of such measurements comprises the following steps:
Step 1: A compound to be tested, FAAH and a fatty acid amide as a substrate are provided.
Step 2: The compound to be tested, FAAH and the substrate are mixed and subjected to an enzymatic reaction.
Step 3: A liquid reaction mixture obtained from Step 2 is brought into contact with a resin having a polar group so that the fatty acid amide is adsorbed onto the resin.
Step 4: The fatty acid amide adsorbed on the resin is quantified.

The FAAH can be obtained by, for example, extraction and purification from natural animal tissues or cells by a known method. It can also be obtained by extraction and purification from cells in which the FAAH gene is introduced and FAAH is expressed according to a known method. This FAAH may be selected according to a particular purpose. For example, the FAAH may be that of mammal origin such as human origin.

As the "fatty acid amide as a substrate", fatty acid amides which can serve as the substrate for FAAH may be appropriately selected, and among those, N-acylated ethanolamine formed from a fatty acid such as medium-chained fatty acid (fatty acid having 8 or more carbon atoms) and long-chained fatty acid (fatty acid having 12 or more carbon atoms), and ethanolamine is preferred, anandamide being particularly preferred. The upper limit of the number of carbon atoms in such a fatty acid is not particularly limited, but the number is preferably not more than 24. Also, such fatty acid may be either saturated or unsaturated, but in particular, fatty acids of polyvalent unsaturated fatty acids are preferred. When N-acylated ethanolamine is hydrolyzed with FAAH, a fatty acid and ethanolamine are produced. For example, in the case of anandamide, arachidonic acid and ethanolamine are produced. It is desirable that such enzymatic reaction is carried out under appropriate conditions, for example, in a reaction buffer at pH 8 to 10 at a temperature of 20° C. to 45° C. for 10 minutes to 1 hour.

In case that the reaction has proceeded, the thus obtained liquid reaction mixture contains an unreacted fatty acid amide, a fatty acid and ethanolamine.

Examples of the "resin having a polar group" which is contacted with such liquid reaction mixture include nitrocellulose and polyvinylidene fluoride (PVDF) (e.g., Immobilon). Such resin may be not necessarily a single compound, and mixtures of nitrocellulose and cellulose (e.g., HA-filter, Millipore Corp.) and the like are used suitably.

The form of the "resin having a polar group" is not particularly limited, but a membrane having micropores is particularly preferred.

When the above-described liquid reaction mixture is brought into contact with the "resin having a polar group", the unreacted fatty acid amide and the fatty acid produced by the reaction are adsorbed onto the resin, whereas ethanolamine produced by the reaction is not adsorbed onto the resin. Thus, the two substance groups can be highly separated. Specifically, in the case of a microporous membrane made of a basic resin, the two substance groups can be easily separated by eliminating a liquid containing ethanolamine by pressurization or suction. In this case, a commercially available plate equipped with a plurality of such membranes (e.g., 96-well MultiScreen-HA filter plate, Millipore Corp.) can be used conveniently.

After separating ethanolamine produced by the reaction from the unreacted fatty acid amide and the fatty acid produced by the reaction in this manner, the FAAH inhibitory activity of the substance to be tested can be measured by quantifying the unreacted fatty acid amide and/or ethanolamine.

This quantification can be carried out easily by using, for example, a fatty acid amide labeled with a radioisotope (e.g., ethanolamine 1-$^3$H) or the like as the substrate. That is, for example, in the case that ethanolamine 1-$^3$H is used, because unreacted ethanolamine 1-$^3$H and arachidonic acid are present on the resin, while [$^3$H]-ethanolamine is present in the liquid, the two substance groups may be separated as described above, and then the amount of radiation of at least one of the groups may be measured with a scintillation counter.

Herein, measurement of the FAAH activity according to the above-described method will be easily understood by a person skill in the art.

Further, sleep action can be evaluated by orally administrating a test compound to a rat, measuring the electroencephalogram (EEG) and electromyogram (EMG) from immediately after administration, and analyzing the resulting EEG and EMG for change in sleep-wake time during the measuring period with an EEG analyzing program, SleepSing Ver. 2 (Kissei Comtech).

The compound of the present invention is low in toxicity, and it can be administered as it is or as a pharmaceutical composition in a suitable dosage form obtained by mixing with a pharmacologically acceptable carrier, orally or parenterally (e.g., topical, intravenous drip infusion, rectal, intraarticular administration) to human or other mammals (e.g., rat, rabbit, sheep, pig, cow, cat, dog, monkey, etc.).

Herein, as the pharmacologically acceptable carrier, a variety of organic or inorganic carrier materials that are conventionally used as materials used for preparation can be used, and they are incorporated as excipient, lubricant, binder or disintegrant in solid preparations; and as solvent, solubilizing agent, suspending agent, isotonic agent, buffer, soothing agent or the like in liquid preparations. In addition, preparation additives such as antiseptic, antioxidant, colorant or sweetener can be also used, if necessary.

Examples of the dosage form of the above-described pharmaceutical composition include oral preparations such as tablet, capsule (including soft capsule and microcapsule), granule, powder, syrup, emulsion and suspension; and parenteral preparations such as injectable preparation (e.g., subcutaneous injection, intradermal injection, intravenous injection, intramuscular injection, intraperitoneal injection, intraarticular injection, etc.), external preparation (e.g., transnasal preparation, transdermal preparation, ointment, etc.), suppository (e.g., rectal suppository, vaginal suppository, etc.), pellet, drip infusion, and sustained release preparation (e.g., sustained release microcapsule, etc.). These can be safely administered orally or parenterally.

The pharmaceutical composition can be prepared by a method conventionally used in the art of formulation technology, for example, a method described in the Japanese Pharmacopeia. Hereinafter, specific methods for formulation will be described in detail. The content of compound (I) or (I') of the present invention in the pharmaceutical composition may vary depending on the dosage form, amount of the compound to be administered and the like, but it is, for example, about 0.1 to 100% by weight.

Specifically, an injectable preparation is prepared by dissolving, suspending or emulsifying the active ingredient in an aqueous solvent (e.g., distilled water, physiologic saline, Ringer's solution, etc.) or an oily solvent (e.g., vegetable oil such as olive oil, sesame oil, cotton seed oil or corn oil, propylene glycol, etc.) together with dispersant (e.g., Polysorbate 80, polyoxyethylene hydrogenated castor oil 60, polyethylene glycol, carboxymethylcellulose, sodium alginate, etc.), preservative (e.g., methylparaben, propylparaben, benzyl alcohol, chlorobutanol, phenol, etc.), isotonic agent (e.g., sodium chloride, glycerin, D-mannitol, D-sorbitol, glucose, etc.), solubilizing agent (e.g., cyclodextrin [e.g., $\alpha$-, $\beta$- or $\gamma$-cyclodextrin, 2-hydroxypropyl-$\beta$-cyclodextrin or methyl-$\beta$-cyclodextrin, etc.]) and the like. At this time, additives such as solubilizing agent (e.g., sodium salicylate, sodium acetate, etc.), stabilizing agent (e.g., human serum albumin, etc.), soothing agent (e.g., benzyl alcohol, etc.) or the like may be used, if necessary. The injectable liquid is usually filled in appropriate ampoules.

Furthermore, the above-described composition may contain other active ingredients as long as they do not cause undesirable interaction upon mixing with the compound of the present invention.

Examples of such other active ingredient include thrombolytic agent (e.g., tissue plasminogen activator, urokinase, etc.), anticoagulant (e.g., Argatroban, warfarin, etc.), Factor 10 inhibitor, thromboxane synthetase inhibitor (e.g., ozagrel, etc.), antioxidant (e.g., edaravone, etc.), antiedema agent (e.g., glycerol, mannitol, etc.), neurogenesis and/or neuroregeneration promoting agent (e.g., Akt/PKB activating agent, GSK-3$\beta$ inhibitor, etc.), acetylcholinesterase inhibitor (e.g., donepezil, rivastigmine, galantamine, zanapezil, etc.), $\beta$-amyloid protein production, secretion, accumulation, aggregation and/or deposition inhibitor [$\beta$-secretase inhibitor (e.g., compound described in WO 98/38156, compounds described in WO 02/2505, WO 02/2506 and WO 02/2512, OM99-2 (WO 01/00663)), $\gamma$-secretase inhibitor, $\beta$-amyloid protein aggregation inhibitor (e.g., PTI-00703, ALZHEMED (NC-531), PPI-368 (JP 11-514333 A), PPI-558 (JP 2001-500852 A), SKF-74652 (Biochem. J., 340(1), 283-289 (1999))), $\beta$-amyloid vaccine, $\beta$-amyloid cleaving enzyme, etc.], brain-activating drug (e.g., aniracetam, nicergoline, etc.), other therapeutic agent for Parkinson's disease [(e.g., dopamine receptor agonist (L-DOPA, bromocriptine, pergolide, talipexol, pramipexol, cabergoline, adamantadine, etc.), monoamine oxidase (MAO) inhibitor (e.g., deprenyl, selgiline (selegiline), remacemide, riluzole, etc.), anticholinergic agent (e.g., trihexyphenidyl, biperiden, etc.)) COMT inhibitor (e.g., entacapone, etc.)], therapeutic agent for amyotrophic lateral sclerosis (e.g., riluzole, etc., neurotrophic factor, etc.), therapeutic agent for hyperlipidemia such as cholesterol-lowering drug [statins (e.g., pravastatin sodium, atorvastatin, simvastatin, lovastatin, etc.), fibrates (e.g., clofibrate, etc.), squalene synthetase inhibitor], therapeutic agent for abnormal behavior, wandering or the like associated with progress of dementia (e.g., sedative, anxiolytic, etc.), apoptosis inhibitor (e.g., CPI-1189, IDN-6556, CEP-1347, etc.), neuronal differentiation and/or regeneration promoting agent (e.g., leteprinim, xaliproden (SR-57746-A), SB-216763, etc.), antihypertensive drug, antidiabetic drug, antidepressant, anxiolytic, non-steroidal anti-inflammatory drug (e.g., meloxicam, tenoxicam, indomethacin, ibuprofen, celecoxib, rofecoxib, aspirin, indomethacin, etc.), disease-modifying antirheumatic drug (DMARDs), anticytokine drug (e.g., TNF inhibitor, MAP kinase inhibitor, etc.), steroid drug (e.g., dexamethasone, hexestrol, cortisone acetate, etc.), sexual hormone or its derivatives (e.g., progesterone, estradiol, estradiol benzoate, etc.), parathyroid hormone (PTH), calcium receptor antagonist, hypnotic (benzodiazepines, non-benzodiazepines) and the like.

The above-described other active ingredient and the compound of the present invention or a salt thereof may be used in combination by mixing them according to a method known per se and formulating into one pharmaceutical composition (e.g., tablet, powder, granule, capsule (including soft capsule), liquid, injection, suppository, sustained release preparation, etc.). Alternatively, they may be formulated into separate preparations and administered to a same subject simultaneously or separately at time interval(s).

In addition, the medicine of the present invention can be used in combination therapy with other therapeutic methods, without being limited in the type of drug. For example, in case of cerebrovascular disorder, the medicine can be used in combination with hypothermia or brain hypothermia, cerebral thrombectomy, cerebral embolectomy or the like, and in case of neurodegenerative disease such as Alzheimer's disease or Parkinson's disease, the medicine can be used in combination with a therapeutic method such as neural stem cell transplantation, without being limited to the mentioned examples.

Dosage of the compound of the present invention may vary depending on subject of administration, disease to be treated, symptoms, administration route or the like. For example, for treatment and/or prevention of cerebrovascular disorder in an adult, usually about 0.01 to 20 mg/kg of body weight, preferably about 0.1 to 10 mg/kg of body weight, more preferably about 0.1 to 5 mg/kg of body weight of the compound of the present invention as active ingredient is administered conveniently in the form of an injectable preparation about 1 to 5 times daily, and preferably about 1 to 3 times daily. In the case of other parenteral administration and oral administration, dosage equivalent to the above-described amount for injection can be administered. When symptoms are particularly severe, the dosage may be increased in accordance with the symptoms.

Hereinafter, the present invention will be illustrated in more detail with reference to Examples, Reference Examples and Experimental Examples.

EXAMPLE 1

4-Biphenyl-3-yl-N-pyridin-3-ylpiperazine-1-carboxamide

A mixed solution of 2,2,2-trichloroethyl pyridin-3-ylcarbamate (249 mg, 0.923 mmol), 1-biphenyl-3-ylpiperazine (200 mg, 0.839 mmol) and diisopropylethylamine (0.292 ml, 1.68 mmol) in dimethylsulfoxide (2.5 ml) was stirred at 70° C. for 12 hours. To the reaction solution was added water, and extracted with ethyl acetate. The extract was washed with water, dried over anhydrous magnesium sulfate, and the solvent was distilled away under reduce pressure. The residue was purified by silica gel column chromatography (ethyl acetate), and then recrystallized from a mixed solvent of hexane and ethyl acetate to give the titled compound (176 mg, 58.6%) as solid product.

$^1$H-NMR (CDCl$_3$) δ; 3.30-3.34 (4H, m), 3.70-3.73 (4H, m), 6.61 (1H, s), 6.92-6.95 (1H, m), 7.13-7.15 (2H, m), 7.23-7.27 (1H, m), 7.33-7.46 (4H, m), 7.56-7.59 (2H, m), 7.99-8.02 (1H, m), 8.29-8.30 (1H, m), 8.45-8.46 (1H, m).

EXAMPLE 2

4-Biphenyl-3-yl-N-(3,4-dimethylisoxazol-5-yl)piperazine-1-carboxamide

A mixed solution of 2,2,2-trichloroethyl(3,4-dimethylisoxazol-5-yl)carbamate (265 mg, 0.923 mmol), 1-biphenyl-3-ylpiperazine (200 mg, 0.839 mmol) and diisopropylethylamine (0.292 ml, 1.68 mmol) in dimethylsulfoxide (2.5 ml) was stirred at 70° C. for 14 hours. To the reaction solution was added water, and extracted with ethyl acetate. The extract was washed with water, dried over anhydrous magnesium sulfate, and the solvent was distilled away under reduce pressure. The residue was purified by silica gel column chromatography (ethyl acetate:hexane=1:1), and then recrystallized from a mixed solvent of hexane and tetrahydrofuran to give the titled compound (198 mg, 62.6%) as solid product.

$^1$H-NMR (CDCl$_3$) δ; 1.89 (3H, s), 2.19 (3H, s), 3.28-3.32 (4H, m), 3.66-3.70 (4H, m), 6.72 (1H, br s), 6.90-6.94 (1H, m), 7.12-7.15 (2H, m), 7.32-7.46 (4H, m), 7.56-7.59 (2H, m).

EXAMPLE 3

N-[6-(Acetylamino)pyridin-3-yl]-4-biphenyl-3-ylpiperazine-1-carboxamide

A mixed solution of 2,2,2-trichloroethyl[6-(acetylamino)pyridin-3-yl]carbamate (301 mg, 0.923 mmol), 1-biphenyl-3-ylpiperazine (200 mg, 0.839 mmol) and diisopropylethylamine (0.292 ml, 1.68 mmol) in dimethylsulfoxide (2.5 ml) was stirred at 70° C. for 14 hours. To the reaction solution was added water, and extracted with ethyl acetate. The extract was washed with water, dried over anhydrous magnesium sulfate, and the solvent was distilled away under reduce pressure. The residue was recrystallized from a mixed solvent of hexane and tetrahydrofuran to give the titled compound (62.6 mg, 18.0%) as solid product.

$^1$H-NMR (DMSO-d$_6$) δ; 2.06 (3H, s), 3.24-3.28 (4H, m), 3.61-3.63 (4H, m), 6.98-7.02 (1H, m), 7.08-7.10 (1H, m), 7.21 (1H, br s), 7.33-7.38 (2H, m), 7.43-7.48 (2H, m), 7.65-7.68 (2H, m), 7.79-7.83 (1H, m), 7.95-7.98 (1H, m), 8.41-8.42 (1H, m), 8.73 (1H, s), 10.33 (1H, s).

EXAMPLE 4

4-(4-Phenylpyridin-2-yl)-N-pyridin-3-ylpiperazine-1-carboxamide (1) 2-Bromo-4-phenylpyridine To a solution of 2-dimethylaminoethanol (5.60 g, 62.8 mmol) in hexane (80 ml) was added dropwise 1.6N hexane solution of n-butyl lithium (78.5 ml, 125 mmol) under ice-cooling, and stirred at 0° C. for 30 minutes. Then, 4-phenylpyridine (3.24 g, 20.8 mmol) was added thereto, and stirred at 0° C. for 1 hour. After cooling the reaction solution to −78° C., a solution of carbon tetrabromide (25.0 g, 75.4 mmol) in hexane (40 ml) was added thereto, and stirred at −78° C. for 1 hour, then at room temperature for 1 hour. To the reaction solution was added water under ice-cooling, and extracted with ether. The extract was dried over anhydrous magnesium sulfate, and the solvent was distilled away under reduce pressure. The residue was purified by silica gel column chromatography (hexane:ethyl acetate=1:1) to give the titled compound 2.21 g (45.4%) as solid product.

$^1$H-NMR (CDCl$_3$) δ; 7.45-7.53 (4H, m), 7.60-7.63 (2H, m), 7.70-7.71 (1H, m), 8.40-8.42 (1H, m).

(2) tert-Butyl 4-(4-phenylpyridin-2-yl)piperazine-1-carboxylate

A solution of 2-bromo-4-phenylpyridine (1.34 g, 5.72 mmol), 1-(tert-butoxycarbonyl)piperazine (3.19 g, 17.2 mmol) and pyridine (20 ml) was stirred at 125° C. for 7 days, and the solvent was distilled away under reduce pressure. To the residue was added water, and extracted with ethyl acetate. The extract was washed with water, and the solvent was distilled away under reduce pressure. The residue was purified by silica gel column chromatography (hexane:ethyl acetate=2:1) to give the titled compound 390 mg (20.1%) as solid product.

$^1$H-NMR (CDCl$_3$) δ; 1.49 (9H, s), 3.58 (8H, s), 6.81 (1H, s), 6.85-6.88 (1H, m), 7.38-7.48 (3H, m), 7.56-7.60 (2H, m), 8.23 (1H, d, J=6.3 Hz)

(3) 1-(4-Phenylpyridin-2-yl)piperazine

A solution of tert-butyl 4-(4-phenylpyridin-2-yl)piperazine-1-carboxylate (390 mg, 1.15 mmol) and 2N methanol solution of hydrogen chloride (30 ml) was stirred at room temperature for 4 hours, and the solvent was distilled away under reduce pressure. To the residue was added 1N aqueous solution of sodium hydroxide (10 ml), extracted with chloroform (10 ml), and the extract was dried over anhydrous magnesium sulfate, and then the solvent was distilled away under reduce pressure to give the titled compound 275 mg (100%) as an oil product.

$^1$H-NMR (CDCl$_3$) δ; 1.60 (1H, br s), 3.00-3.04 (4H, m), 3.56-3.59 (4H, m), 6.82 (1H, s), 6.85-6.87 (1H, m), 7.41-7.49 (3H, m), 7.57-7.62 (2H, m), 8.24 (1H, d, J=5.1 Hz).

(4) 4-(4-Phenylpyridin-2-yl)-N-pyridin-3-ylpiperazine-1-carboxamide

A solution of 2,2,2-trichloroethyl pyridin-3-ylcarbamate (113 mg, 0.418 mmol), 1-(4-phenylpyridin-2-yl)piperazine (100 mg, 0.418 mmol), diisopropylethylamine (0.146 ml, 0.836 mmol) and dimethylsulfoxide (2 ml) was stirred at 70° C. for 12 hours, then the reaction solution was poured into water, and extracted with ethyl acetate. The extract was washed with water, and dried over anhydrous magnesium sulfate. The solvent was distilled away under reduce pressure, and the residue was purified by basic silica gel column chromatography (ethyl acetate) to give the titled compound as solid product. This was recrystallized from a mixed solvent of hexane and ethyl acetate to give the titled compound 67.2 mg (44.8%) as solid product.

$^1$H-NMR (CDCl$_3$) δ; 3.68-3.76 (8H, m), 6.58 (1H, s), 6.83 (1H, s), 6.90-6.92 (1H, m), 7.23-7.27 (1H, m), 7.41-7.50 (3H, m), 7.57-7.61 (2H, m), 7.98-8.02 (1H, m), 8.24 (1H, d, J=5.7 Hz), 8.28-8.30 (1H, m), 8.46 (1H, d, J=2.1 Hz).

EXAMPLE 5

N-(3,4-Dimethylisoxazol-5-yl)-4-(4-phenylpyridin-2-yl)piperazine-1-carboxamide A solution of 2,2,2-trichloroethyl(3,4-dimethylisoxazol-5-yl)carbamate (120 mg, 0.418 mmol), 1-(4-phenylpyridin-2-yl)piperazine (100 mg, 0.418 mmol), diisopropylethylamine (0.146 ml, 0.836 mmol) and dimethylsulfoxide (2 ml) was stirred at 70° C. for 3 hours, then the reaction solution was poured into water, and extracted with ethyl acetate. The extract was washed with water, and dried over anhydrous magnesium sulfate. The solvent was distilled away under reduce pressure, and the residue was recrystallized from ethyl acetate to give the titled compound 58.0 mg (36.7%) as solid product.

$^1$H-NMR (CDCl$_3$) δ; 1.90 (3H, s), 2.20 (3H, s), 3.67-3.74 (8H, m), 6.57 (1H, s), 6.82 (1H, s), 6.90-6.92 (1H, m), 7.41-7.49 (3H, m), 7.58-7.61 (2H, m), 8.24 (1H, d, J=5.1 Hz).

EXAMPLE 6

4-(4-Phenylpyridin-2-yl)-N-pyridazin-3-ylpiperazine-1-carboxamide

A solution of 2,2,2-trichloroethyl pyridazin-3-ylcarbamate (113 mg, 0.418 mmol), 1-(4-phenylpyridin-2-yl)piperazine (75.0 mg, 0.313 mmol), diisopropylethylamine (0.146 ml, 0.836 mmol) and dimethylsulfoxide (2 ml) was stirred at 70° C. for 3 hours, then the reaction solution was poured into water, and extracted with ethyl acetate. The extract was washed with water, and dried over anhydrous magnesium sulfate. The solvent was distilled away under reduce pressure, and the residue was recrystallized from ethyl acetate to give the titled compound 52.0 mg (46.0%) as solid product.

$^1$H-NMR (DMSO-d$_6$) δ; 3.65 (8H, s), 6.97 (1H, d, J=5.1 Hz), 7.11 (1H, s), 7.44-7.60 (4H, m), 7.76-7.79 (2H, m), 7.99-8.03 (1H, m), 8.18 (1H, d, J=5.1 Hz), 8.83-8.85 (1H, m), 9.96 (1H, br s).

EXAMPLE 7

N-(3,4-Dimethylisoxazol-5-yl)-4-(5-phenylpyridin-2-yl)piperazine-1-carboxamide

(1) tert-Butyl 4-(5-bromopyridin-2-yl)piperazine-1-carboxylate

A mixed solution of 2,5-dibromopyridine (6.36 g, 26.8 mmol), 1-(tert-butoxycarbonyl)piperazine (5.00 g, 26.8 mmol) and pyridine (100 ml) was stirred at 125° C. for 12 hours, and the solvent was distilled away under reduce pressure. The residue was poured into water, and extracted with ethyl acetate. The extract was washed with water, dried over anhydrous magnesium sulfate, and the solvent was distilled away under reduce pressure. The residue was purified by silica gel column chromatography (hexane:ethyl acetate=10:1) to give the titled compound 3.62 g (39.5%) as solid product.

$^1$H-NMR (CDCl$_3$) δ; 1.48 (9H, s), 3.47-3.55 (8H, m), 6.52-6.56 (1H, m), 7.52-7.56 (1H, m), 8.18-8.20 (1H, m).

(2) tert-Butyl 4-(5-phenylpyridin-2-yl)piperazine-1-carboxylate

A mixed solution of tert-butyl 4-(5-bromopyridin-2-yl)piperazine-1-carboxylate (1.00 g, 2.92 mmol), phenylboronic acid (535 mg, 4.38 mmol), ethanol (2.5 ml), 2N aqueous solution of sodium carbonate (12 ml), tetrakis(triphenylphosphine)palladium (404 mg, 0.350 mmol) and toluene (23 ml) was stirred at 95° C. for 12 hours under a nitrogen atmosphere, and the solvent was distilled away under reduce pressure. The residue was poured into water, and extracted with ethyl acetate. The extract was washed with water, dried over anhydrous magnesium sulfate, and the solvent was distilled away under reduce pressure. The residue was purified by silica gel column chromatography (hexane:ethyl acetate=2:1) to give the titled compound 800 mg (80.7%) as solid product.

$^1$H-NMR (CDCl$_3$) δ; 1.49 (9H, s), 3.57 (8H, s), 6.72 (1H, d, J=8.7 Hz), 7.29-7.54 (5H, m), 7.73 (1H, dd, J=8.7, 2.4 Hz), 8.45 (1H, d, J=2.4 Hz).

(3) 1-(5-Phenylpyridin-2-yl)piperazine

A mixed solution of tert-butyl 4-(5-phenylpyridin-2-yl)piperazine-1-carboxylate (800 mg, 2.36 mmol), 2N methanol solution of hydrogen chloride (5 ml) and ethyl acetate (5 ml) was stirred at room temperature for 4 hours, and the solvent was distilled away under reduce pressure. To the residue was added 1N aqueous solution of sodium hydroxide (10 ml), and the titled compound 520 mg (92.1%) was collected by filtration as a solid product.

$^1$H-NMR (CDCl$_3$) δ; 1.68 (1H, br s), 2.99-3.03 (4H, m), 3.54-3.57 (4H, m), 6.72 (1H, d, J=9.0 Hz), 7.28-7.54 (5H, m), 7.72 (1H, dd, J=9.0, 2.4 Hz), 8.45 (1H, d, J=2.4 Hz).

(4) N-(3,4-Dimethylisoxazol-5-yl)-4-(5-phenylpyridin-2-yl)piperazine-1-carboxamide A solution of 2,2,2-trichloroethyl(3,4-dimethylisoxazol-5-yl)carbamate (251 mg, 0.872 mmol), 1-(5-phenylpyridin-2-yl)piperazine (200 mg, 0.872 mmol), diisopropylethylamine (0.304 ml, 1.74 mmol) and dimethylsulfoxide (4 ml) was stirred at 70° C. for 12 hours, then the reaction solution was poured into water, and extracted with ethyl acetate. The extract was washed with water, and dried over anhydrous magnesium sulfate. The solvent was distilled away under reduce pressure, and the residue was recrystallized from ethyl acetate to give the titled compound 150 mg (45.6%) as solid product.

$^1$H-NMR (DMSO-$d_6$) δ; 1.76 (3H, s), 2.13 (3H, s), 3.59 (8H, br s), 6.98 (1H, d, J=9.0 Hz), 7.28-7.33 (1H, m), 7.41-7.46 (2H, m), 7.62-7.64 (2H, m), 7.89 (1H, dd, J=9.0, 2.1 Hz), 8.47 (1H, d, J=2.1 Hz), 9.25 (1H, s).

EXAMPLE 8

4-(5-Phenylpyridin-2-yl)-N-pyridin-3-ylpiperazine-1-carboxamide

A solution of 2,2,2-trichloroethyl pyridin-3-ylcarbamate (235 mg, 0.872 mmol), 1-(5-phenylpyridin-2-yl)piperazine (200 mg, 0.872 mmol), diisopropylethylamine (0.3047 ml, 1.74 mmol) and dimethylsulfoxide (4 ml) was stirred at 70° C. for 12 hours, then the reaction solution was poured into water, and extracted with ethyl acetate. The extract was washed with water, and dried over anhydrous magnesium sulfate. The solvent was distilled away under reduce pressure, and the residue was recrystallized from ethyl acetate to give the titled compound 47 mg (47.0%) as solid product.

$^1$H-NMR (DMSO-$d_6$) δ; 3.62 (8H, s), 6.99 (1H, d, J=8.7 Hz), 7.26-7.33 (2H, m), 7.41-7.46 (2H, m), 7.62-7.65 (2H, m), 7.88-7.93 (2H, m), 8.15-8.17 (1H, m), 8.48 (1H, d, J=2.4 Hz), 8.67 (1H, d, J=2.4 Hz), 8.82 (1H, s).

EXAMPLE 9

4-Biphenyl-3-yl-N-pyridazin-3-ylpiperazine-1-carboxamide

A mixed solution of 2,2,2-trichloroethyl pyridazin-3-ylcarbamate (250 mg, 0.923 mmol), 1-biphenyl-3-ylpiperazine (200 mg, 0.839 mmol) and diisopropylethylamine (0.292 ml, 1.68 mmol) in dimethylsulfoxide (2.5 ml) was stirred at 70° C. for 12 hours. Water was poured into the reaction solution, and extracted with ethyl acetate. The extract was washed with water, dried over anhydrous magnesium sulfate, and the solvent was distilled away under reduce pressure. The residue was purified by silica gel column chromatography (ethyl acetate) to give the titled compound 60.3 mg (20.0%) as solid product.

$^1$H-NMR (DMSO-$d_6$) δ; 3.22-3.31 (4H, m), 3.62-3.75 (4H, m), 6.95-7.03 (1H, m), 7.09 (1H, d, J=7.6 Hz), 7.21 (1H, s), 7.27-7.39 (2H, m), 7.45 (2H, t, J=7.6 Hz), 7.58 (1H, dd, J=9.1, 4.5 Hz), 7.66 (2H, d, J=8.0 Hz), 8.02 (1H, d, J=9.1 Hz), 8.85 (1H, d, J=4.5 Hz), 9.96 (1H, br s).

EXAMPLE 10

N-[4-(Acetylamino)phenyl]-4-[3-(3-thienyl)phenyl]piperazine-1-carboxamide

(1) 1-[3-(3-Thienyl)phenyl]piperazine

A mixed solution of 1-(3-bromophenyl)-piperazine (300 mg, 1.24 mmol), 3-thienylboronic acid (239 mg, 1.87 mmol), tetrakis(triphenylphosphine)palladium (173 mg, 0.149 mmol), 2N aqueous solution of sodium carbonate (4.98 ml, 9.95 mmol), and toluene (12 ml) was stirred at 95° C. for 15 hours under a nitrogen atmosphere. After cooling to room temperature, water was poured into the reaction solution, and extracted with ethyl acetate. The extract was washed with water, dried over anhydrous magnesium sulfate, and the solvent was distilled away under reduce pressure. The residue was purified by basic silica gel column chromatography (ethyl acetate) to give the titled compound 254 mg (83.5%) as an oil.

$^1$H-NMR (CDCl$_3$) δ; 3.03-3.07 (4H, m), 3.18-3.21 (4H, m), 6.85-6.89 (1H, m), 7.07-7.10 (1H, m), 7.13-7.15 (1H, m), 7.26-7.32 (1H, m), 7.36-7.38 (2H, m), 7.41-7.43 (1H, m).

(2) N-[4-(Acetylamino)phenyl]-4-[3-(3-thienyl)phenyl]piperazine-1-carboxamide A mixed solution of 2,2,2-trichloroethyl[6-(acetylamino)pyridin-3-yl]carbamate (147 mg, 0.450 mmol), 1-[3-(3-thienyl)phenyl]piperazine (100 mg, 0.409 mmol) and diisopropylethylamine (0.143 ml, 0.818 mmol) in dimethylsulfoxide (1.5 ml) was stirred at 70° C. for 15 hours. Water was poured into the reaction solution, and extracted with ethyl acetate. The extract was washed with water, dried over anhydrous magnesium sulfate, and the solvent was distilled away under reduce pressure. The residue was purified by silica gel column chromatography (ethyl acetate), and recrystallized from a mixed solvent of hexane and tetrahydrofuran to give the titled compound 85.5 mg (51.5%) as solid product.

$^1$H-NMR (DMSO-$d_6$) δ; 2.06 (3H, s), 3.23-3.26 (4H, m), 3.58-3.64 (4H, m), 6.91-6.94 (1H, m), 7.14-7.17 (1H, m), 7.24-7.29 (2H, m), 7.56-7.63 (2H, m), 7.79-7.87 (2H, m), 7.95-7.98 (1H, m), 8.41-8.42 (1H, m), 8.73 (1H, s), 10.33 (1H, s).

EXAMPLE 11

N-(3,4-Dimethylisoxazol-5-yl)-4-[3-(3-thienyl)phenyl]piperazine-1-carboxamide A mixed solution of 2,2,2-trichloroethyl(3,4-dimethylisoxazol-5-yl)carbamate (129 mg, 0.450 mmol), 1-[3-(3-thienyl)phenyl]piperazine (100 mg, 0.409 mmol) and diisopropylethylamine (0.143 ml, 0.818 mmol) in dimethylsulfoxide (1.5 ml) was stirred at 70° C. for 15 hours. Water was poured into the reaction solution, and extracted with ethyl acetate. The extract was washed with water, dried over anhydrous magnesium sulfate, and the solvent was distilled away under reduce pressure. The residue was purified by silica gel column chromatography (hexane:ethyl acetate=3:7), and recrystallized from a mixed solvent of hexane and tetrahydrofuran to give the titled compound 30.7 mg (19.6%) as solid product.

$^1$H-NMR (CDCl$_3$) δ; 1.90 (3H, s), 2.20 (3H, s), 3.27-3.30 (4H, m), 3.66-3.70 (4H, m), 6.69 (1H, br s), 6.86-6.90 (1H, m), 7.14-7.16 (2H, m), 7.30-7.40 (3H, m), 7.43-7.45 (1H, m).

EXAMPLE 12

N-Pyridin-3-yl-4-[3-(3-thienyl)phenyl]piperazine-1-carboxamide

A mixed solution of 2,2,2-trichloroethyl pyridin-3-ylcarbamate (303 mg, 1.13 mmol), 1-[3-(3-thienyl)phenyl]piperazine (250 mg, 1.02 mmol) and diisopropylethylamine (0.356 ml, 2.05 mmol) in dimethylsulfoxide (3.5 ml) was stirred at 70° C. for 3 days. Water was poured into the reaction solution, and extracted with ethyl acetate. The extract was washed with water, dried over anhydrous magnesium sulfate, and the solvent was distilled away under reduce pressure. The residue was purified by silica gel column chromatography (ethyl acetate), and recrystallized from a mixed solvent of hexane and tetrahydrofuran to give the titled compound 139 mg (37.3%) as solid product.

$^1$H-NMR (CDCl$_3$) δ; 3.28-3.31 (4H, m), 3.69-3.73 (4H, m), 6.76 (1H, br s), 6.86-6.90 (1H, m), 7.14-7.16 (2H, m), 7.23-7.27 (1H, m), 7.29-7.40 (3H, m), 7.43-7.44 (1H, m), 7.98-8.02 (1H, m), 8.27-8.29 (1H, m), 8.45-8.46 (1H, m).

EXAMPLE 13

4-[3-(3-Furyl)phenyl]-N-pyridin-3-ylpiperazine-1-carboxamide

(1) 1-[3-(3-Furyl)phenyl]piperazine

A mixed solution of 1-(3-bromophenyl)-piperazine (100 mg, 0.415 mmol), 3-furylboronic acid (69.6 mg, 0.622 mmol), tetrakis(triphenylphosphine)palladium (57.5 mg, 0.050 mmol), 2N aqueous solution of sodium carbonate (1.66 ml, 3.32 mmol) in toluene (4.0 ml) was stirred at 95° C. for 14 hours under a nitrogen atmosphere. After cooling to room temperature, water was poured into the reaction solution, and extracted with ethyl acetate. The extract was washed with water, dried over anhydrous magnesium sulfate, and the solvent was distilled away under reduce pressure. The residue was purified by basic silica gel column chromatography (ethyl acetate) to give the titled compound 45.4 mg (47.9%) as an oil.

$^1$H-NMR (CDCl$_3$) δ; 3.02-3.05 (4H, m), 3.16-3.19 (4H, m), 6.68-6.69 (1H, m), 6.82-6.86 (1H, m), 6.98-7.04 (2H, m), 7.24-7.29 (1H, m), 7.45-7.47 (1H, m), 7.70-7.71 (1H, m).

(2) 4-[3-(3-Furyl)phenyl]-N-pyridin-3-ylpiperazine-1-carboxamide

A mixed solution of 2,2,2-trichloroethyl pyridin-3-ylcarbamate (279 mg, 1.04 mmol), 1-[3-(3-furyl)phenyl]piperazine (215 mg, 0.942 mmol) and diisopropylethylamine (0.328 ml, 1.88 mmol) in dimethylsulfoxide (3.0 ml) was stirred at 70° C. for 3 days. Water was poured into the reaction solution, and extracted with ethyl acetate. The extract was washed with water, dried over anhydrous magnesium sulfate, and the solvent was distilled away under reduce pressure. The residue was purified by silica gel column chromatography (ethyl acetate), and recrystallized from a mixed solvent of hexane and ethyl acetate to give the titled compound 147 mg (44.7%) as solid product.

$^1$H-NMR (CDCl$_3$) δ; 3.26-3.30 (4H, m), 3.69-3.73 (4H, m), 6.68-6.69 (1H, m), 6.76 (1H, br s), 6.83-6.87 (1H, m), 7.03-7.07 (2H, m), 7.23-7.32 (2H, m), 7.47-7.48 (1H, m), 7.71-7.72 (1H, m), 7.98-8.01 (1H, m), 8.27-8.29 (1H, m), 8.45-8.46 (1H, m).

EXAMPLE 14

4-Biphenyl-4-yl-N-pyridin-3-ylpiperazine-1-carboxamide

A mixed solution of 2,2,2-trichloroethyl pyridin-3-ylcarbamate (249 mg, 0.923 mmol), 1-biphenyl-4-ylpiperazine (200 mg, 0.839 mmol) and diisopropylethylamine (0.292 ml, 1.68 mmol) in dimethylsulfoxide (2.5 ml) was stirred at 70° C. for 16 hours. Water was poured into the reaction solution, and extracted with ethyl acetate. The extract was washed with water, dried over anhydrous magnesium sulfate, and the solvent was distilled away under reduce pressure. The residue was recrystallized from a mixed solvent of hexane and tetrahydrofuran to give the titled compound (163 mg, 54.2%) as solid product.

$^1$H-NMR (CDCl$_3$) δ; 3.29-3.32 (4H, m), 3.70-3.73 (4H, m), 6.72 (1H, br s), 6.98-7.01 (2H, m), 7.23-7.32 (2H, m), 7.39-7.44 (2H, m), 7.52-7.57 (4H, m), 7.99-8.03 (1H, m), 8.28-8.29 (1H, m), 8.46-8.47 (1H, m).

EXAMPLE 15

4-Biphenyl-4-yl-N-(3,4-dimethylisoxazol-5-yl)piperazine-1-carboxamide

A mixed solution of 2,2,2-trichloroethyl(3,4-dimethylisoxazol-5-yl)carbamate (265 mg, 0.923 mmol), 1-biphenyl-4-ylpiperazine (200 mg, 0.839 mmol) and diisopropylethylamine (0.292 ml, 1.68 mmol) in dimethylsulfoxide (2.5 ml) was stirred at 70° C. for 15 hours. Water was poured into the reaction solution, and extracted with ethyl acetate. The extract was washed with water, dried over anhydrous magnesium sulfate, and the solvent was distilled away under reduce pressure. The residue was recrystallized from a mixed solvent of hexane and tetrahydrofuran to give the titled compound (180 mg, 57.1%) as solid product.

$^1$H-NMR (CDCl$_3$) δ; 1.89 (3H, s), 2.20 (3H, s), 3.27-3.30 (4H, m), 3.66-3.70 (4H, m), 6.76 (1H, br s), 7.00 (2H, d, J=8.7 Hz), 7.27-7.32 (1H, m), 7.39-7.44 (2H, m), 7.52-7.57 (4H, m).

Experimental Example 1

Measurement of FAAH Inhibitory Activity (1) Preparation of Enzyme Fraction

The FAAH gene was cloned by PCR. That is, a human brain library was used as a cDNA library, 5'-AAAAGAAT-TCGCCACCATGGTGCAGTACGAGCTGTG-3' [SEQ ID NO:1] and 5'-TTTTGTCGACTCAGGATGACTGCTTTT-3' [SEQ ID NO:2] were used as a primer set, and KOD DNA polymerase (Toyobo Co., Ltd.) was used as a DNA polymerase. One cycle of the reaction comprises 95° C. for 30 sec, 55° C. for 30 sec and 72° C. for 2 min, and 45 cycles of the reaction was carried out to obtain an amplified fragment. The amplified fragment was cleaved with restriction enzymes EcoRI and SalI, and then was inserted into a pMSRα vector which had been cleaved with the same restriction enzymes EcoRI and SalI to obtain a pMSRα-human FAAH. A cell line CHO-K1 and the above-obtained plasmid were subjected to a method known per se to prepare the cell line CHO-K1/human FAAH in which human FAAH was stably expressed. The CHO-K1/human FAAH was cultured in a CO$_2$ incubator at 37° C., using a medium (Ham's F-12 medium supplemented with final concentration 10% of fetal bovine serum (FBS) and final concentration 800 μg/ml of G418), and then the cells were harvested. After washing with PBS, the cells were suspended in a buffer (10 mM Tris, 1 mM EDTA and 10 mM $MgCl_2$, all at final concentrations) and disrupted with a Polytron homogenizer. After centrifugation at 900 g, the supernatant was recovered and further centrifuged at 10000 g. A pellet obtained therefrom was suspended in M-PER (Catalog No. 78501; PIERCE) to give an enzyme fraction.

(2) Enzymatic Reaction

Using a white walled 96-well plate (Coster Corp.), the test compound at various concentrations, 60 ng of the enzyme fraction and the substrate anandamide [ethanolamine 1-$^3$H] (final concentration 25 nM) were reacted in 50 μl of a reaction buffer (125 mM Tris-HCl (pH 9.0), 1 mM EDTA, 0.4 mM HEPES, 0.2% glycerol and 0.02% Triton X-100, all at final concentrations) at 37° C. for 30 minutes. The reaction mixture was transferred to a 96-well MultiScreen-HA filter plate (Millipore Corp.) and then was left to stand overnight at room temperature in order to allow the unreacted substrate to be adsorbed on the filter. The plate was washed with PBS using a MultiScreen Vacuum Manifold (Millipore Corp.) and dried. To each well, 50 μl of liquid scintillation cocktail was added and stirred, and then counting was performed with a TopCount (Perkin-Elmer Corp.). The count of a sample containing a solvent instead of the test compound was taken as 0%, and the count at zero time was taken as 100%, to calculate the inhibitory activity of the compound. The results are presented in Table 1.

TABLE 1

| Example No. | Human FAAH Inhibition Rate at 1 μM (%) |
|---|---|
| 1 | 103 |
| 2 | 104 |
| 3 | 101 |
| 4 | 74 |
| 5 | 94 |
| 6 | 91 |
| 7 | 102 |
| 8 | 98 |
| 9 | 105 |
| 10 | 108 |
| 11 | 100 |
| 12 | 104 |
| 13 | 104 |
| 14 | 101 |
| 15 | 102 |

It can be seen from the results of Table 1 that the compound of the invention has excellent FAAH inhibitory activity.

Experimental Example 2

Cerebroprotective Effect in a Rat Cerebral Ischemic Model

By intravenous administration, the inhibitory effect of test compound on cerebral infarct volume in a rat local cerebral ischemic model is examined. For the cerebral ischemic model, 8 weeks-old male SD rats (CLEA Japan, Inc.) are used to generate a middle cerebral artery occlusion model (Kiyota, et al., Experimental Brain Research, 95, 388-396 (1993)). That is, under halothane anesthesia, a silicone-coated plug was inserted into the rat from the right common carotid artery to the origin of middle cerebral artery to induce occlusion for 120 minutes. Test compound is intravenously administered immediately after reperfusion and after 2, 4 and 6 hours, respectively. Two days after the ischemia treatment, the rat brain was extracted, 2 mm-thick slices of anterior maxillary section are prepared therefrom, and the cerebral infarct volume is measured from their TTC-stained images by image analysis.

From the result that the infarct volume of the compound-administered group is smaller compared with that of the vehicle-administered group, it is shown that inhibition of the function of FAAH results in the cerebral infarction inhibitory action.

Experimental Example 3

Test of Sleep Action

Measurement of Electroencephalogram (EEG)

Grids are attached to an acrylic cylindrical cage with 30 cm in diameter and 50 cm in height, at 7 cm from the bottom at 2 cm intervals, and the bottom of the cage is filled with water. A rat is placed on the grids. A test compound is administered orally to the rat. From immediately after administration, EEG and electromyogram (EMG) are measured. The EEG and EMG data obtained are recorded by a bioamplifier built-in recording apparatus, polymate AP1124 (TEAC Instruments Corporation). The EEG and EMG data obtained are analyzed every 4 seconds at a sampling frequency of 1 kHz by using an EEG analyzing program, SleepSing Ver. 2 (Kissei Comtech). Sleep action of a FAAH inhibitor is evaluated by analyzing change in sleep-wake time during the measuring period.

INDUSTRIAL APPLICABILITY

The compound of the present invention has a brain/neuronal cell protective effect, in particular, a brain/neuronal cell protective effect in case of cerebrovascular disorders and head injury. Therefore, the compound of the present invention is useful for a prevention and treatment of diseases in which protection of brain cells and neuronal cells from cell damage is effective prophylactically and therapeutically, preferably cerebrovascular disorders and head injury. Furthermore, the compound of the present invention is useful for a prevention and treatment of sleep disorders.

The invention claimed is:

1. A compound represented by the formula (I):

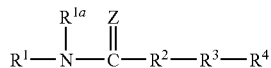 (I)

wherein Z represents an oxygen, $R^1$ represents an isoxazolyl, pyridyl or pyridazinyl, each of which may be substituted with one or more substituents selected from a group consisting of a $C_{1-6}$ alkyl which may be halogenated or oxolated, a $C_{1-6}$ alkoxy which may be halogenated or oxolated, a $C_{1-6}$ acylamino which may be halogenated or oxolated, a N—($C_{1-6}$alkyl)$C_{1-6}$ acylamino, a $C_{1-6}$ acyl which may be halogenated or oxolated, a $C_{1-6}$ alkylamino, a di-$C_{1-6}$ alkylamino, a $C_{1-6}$ alkenyl which may be halogenated or oxolated, a $C_{1-6}$ alkynyl which may be halogenated or oxolated, a $C_{1-6}$ alkyloxycarbonyl, a carbamoyl, carboxy, a $C_{1-6}$ alkylsulfonylamide which may be halogenated or oxolated, a $C_{1-6}$ alkylthio which may be halogenated or oxolated, a $C_{1-6}$ alkylsulfinyl which may be halogenated or oxolated, amino, hydroxyl, a halogen, nitrile, 2-oxopyrrolidin-1-yl, imidazolyl and pyrazolyl, provided that 5-ethyl-2-methoxy-6-methyl-3-pyridinyl is excluded, $R^{1a}$ represents a hydrogen atom, $R^2$ represents piperazin-1,4-diyl which may be substituted with one or more substituents selected from a group consisting of a $C_{1-6}$ alkyl which may be halogenated or oxolated, a $C_{1-6}$ alkoxy which may be halogenated or oxolated, a $C_{1-6}$ acylamino which may be halogenated or oxolated, a N—($C_{1-6}$alkyl) $C_{1-6}$ acylamino, a $C_{1-6}$ acyl which may be halogenated or oxolated, a $C_{1-6}$ alkylamino, a di-$C_{1-6}$ alkylamino, a $C_{1-6}$ alkenyl which may be halogenated or oxolated, a $C_{1-6}$ alkynyl which may be halogenated or oxolated, a $C_{1-6}$ alkyloxycarbonyl, a carbamoyl, carboxy, a $C_{1-6}$ alkylsulfonylamide which may be halogenated or oxolated, a $C_{1-6}$ alkylthio which may be halogenated or oxolated, a $C_{1-6}$ alkylsulfinyl which may be halogenated or oxolated, amino, hydroxyl, a halogen, nitrile and 2-oxopyrrolidin-1-yl, $R^3$ represents a divalent group formed by removing two hydrogen atoms from a benzene or 6-membered aromatic heterocyclic ring containing 1 to 4 heteroatoms selected from oxygen atom, sulfur atom and nitrogen atom in addition to carbon atom, with pyridazin-3,6-diyl excluded, each of which may have one or more substituents selected from a group consisting of a $C_{1-6}$ alkyl which may be halogenated or oxolated, a $C_{1-6}$ alkoxy which may be halogenated or oxolated, a $C_{1-6}$ acylamino which may be halogenated or oxolated, a N—($C_{1-6}$ alkyl)$C_{1-6}$ acylamino, a $C_{1-6}$ acyl which may be halogenated or oxolated, a $C_{1-6}$ alkylamino, a di-$C_{1-6}$ alkylamino, a $C_{1-6}$ alkenyl which may be halogenated or oxolated, a $C_{1-6}$ alkynyl which may be halogenated or oxolated, a $C_{1-6}$ alkyloxycarbonyl, a carbamoyl, carboxy, a $C_{1-6}$ alkylsulfonylamide which may be halogenated or oxolated, a $C_{1-6}$ alkylthio which may be halogenated or oxolated, a $C_{1-6}$ alkylsulfinyl which may be halogenated or oxolated, amino, hydroxy, a halogen and nitrile, and $R^4$ represents a phenyl, thienyl or furyl, each of which may be substituted with one or more substituents selected from a group consisting of a $C_{1-6}$ alkyl which may be halogenated or oxolated, a $C_{1-6}$ alkoxy which may be halogenated or oxolated, a $C_{1-6}$ acylamino which may be halogenated or oxolated, a N—($C_{1-6}$alkyl)$C_{1-6}$ acylamino, a $C_{1-6}$ acyl which may be halogenated or oxolated, a $C_{1-6}$ alkylamino, a di-$C_{1-6}$ alkylamino, a $C_{1-6}$ alkenyl which may be halogenated or oxolated, a $C_{1-6}$ alkynyl which may be halogenated or oxolated, a $C_{1-6}$ alkyloxycarbonyl, a carbamoyl, carboxy, a $C_{1-6}$ alkylsulfonylamide which may be halogenated or oxolated, a $C_{1-6}$ alkylthio which may be halogenated or oxolated, a $C_{1-6}$ alkylsulfinyl which may be halogenated or oxolated, amino, hydroxy, a halogen and nitrile, or a salt thereof.

2. The compound according to claim 1, wherein the divalent group represented by $R^3$ is a group formed by removing two hydrogen atoms from a benzene, pyridine, pyrimidine, pyrazine, triazine, oxazine or thiazine, or a salt thereof.

3. The compound according to claim 1, wherein $R^1$ is isoxazolyl which may be substituted with one or more $C_{1-6}$ alkyl, pyridyl which may be substituted with one or more $C_{1-6}$ acylamino, or pyridazinyl.

4. The compound according to claim 1, wherein $R^3$ is a divalent group represented by formula:

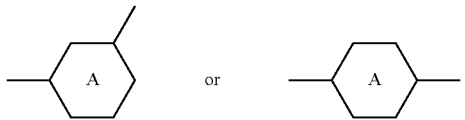

wherein ring A represents benzene, pyridine, pyrimidine, pyrazine, triazine, oxazine or thiazine ring, or a salt thereof.

5. The compound according to claim 1, wherein $R^3$ is 1,3-phenylene, 1,4-phenylene, pyridin-2,4-diyl or pyridin-2,5-diyl, each of which may have one or more substituents selected from a group consisting of a $C_{1-6}$ alkyl which may be halogenated or oxolated, a $C_{1-6}$ alkoxy which may be halogenated or oxolated, a $C_{1-6}$ acylamino which may be halogenated or oxolated, a N—($C_{1-6}$ alkyl)$C_{1-6}$ acylamino, a $C_{1-6}$ acyl which may be halogenated or oxolated, a $C_{1-6}$ alkylamino, a di-$C_{1-6}$ alkylamino, a $C_{1-6}$ alkenyl which may be halogenated or oxolated, a $C_{1-6}$ alkynyl which may be halogenated or oxolated, a $C_{1-6}$ alkyloxycarbonyl, carbamoyl, carboxy, a $C_{1-6}$ alkylsulfonylamide which may be halogenated or oxolated, a $C_{1-6}$ alkylthio which may be halogenated or oxolated, a $C_{1-6}$ alkylsulfinyl which may be halogenated or oxolated, amino, hydroxy, a halogen and nitrile.

6. The compound according to claim 1, which is
4-biphenyl-3-yl-N-pyridin-3-ylpiperazine-1-carboxamide,
4-biphenyl-3-yl-N-(3,4-dimethylisoxazol-5-yl)piperazine-1-carboxamide,
N-[6-(acetylamino)pyridin-3-yl]-4-biphenyl-3-ylpiperazine-1-carboxamide,
4-(4-phenylpyridin-2-yl)-N-pyridin-3-ylpiperazine-1-carboxamide,
N-(3,4-dimethylisoxazol-5-yl)-4-(4-phenylpyridin-2-yl)piperazine-1-carboxamide,
4-(4-phenylpyridin-2-yl)-N-pyridazin-3-ylpiperazine-1-carboxamide,
N-(3,4-dimethylisoxazol-5-yl)-4-(5-phenylpyridin-2-yl)piperazine-1-carboxamide,
4-(5-phenylpyridin-2-yl)-N-pyridin-3-ylpiperazine-1-carboxamide,
4-biphenyl-3-yl-N-pyridazin-3-ylpiperazine-1-carboxamide,
N-[4-(acetylamino)phenyl]-4-[3-(3-thienyl)phenyl]piperazine-1-carboxamide,
N-(3,4-dimethylisoxazol-5-yl)-4-[3-(3-thienyl)phenyl]piperazine-1-carboxamide,
N-pyridin-3-yl-4-[3-(3-thienyl)phenyl]piperazine-1-carboxamide,
4-[3-(3-furyl)phenyl]-N-pyridin-3-ylpiperazine-1-carboxamide,
4-biphenyl-4-yl-N-pyridin-3-ylpiperazine-1-carboxamide, or
4-biphenyl-4-yl-N-(3,4-dimethylisoxazol-5-yl)piperazine-1-carboxamide, or a salt thereof.

7. A pharmaceutical composition comprising the compound according to claim 1 or a salt thereof.

8. A fatty acid amide hydrolase inhibitor comprising a compound according to claim 1, or a salt thereof.

9. A therapeutic agent for sleep disorder, anxiety or depression, or an analgesic agent comprising a compound according to claim 1, or a salt thereof.

10. A method for treating sleep disorder, anxiety or depression, or a method for pain relief, which comprises administering to a subject in need thereof an effective amount of a compound according to claim 1, or a salt thereof.

11. The compound according to claim 1, wherein $R^1$ represents an isoxazolyl which may be substituted with one or more substituents selected from $C_{1-6}$ alkyl, a pyridyl which may be substituted with one or more $C_{1-6}$ acylamino, or a pyridazinyl,
$R^2$ represents a piperazin-1,4-diyl,
$R^3$ is a divalent group represented by formula:

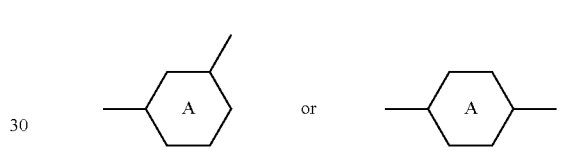

wherein ring A represents benzene, pyridine, pyrimidine, pyrazine, triazine, oxazine or thiazine ring, and $R^4$ represents a phenyl, thienyl or furyl, each of which may be substituted with one or more substituents selected from a group consisting of a $C_{1-6}$ alkyl which may be halogenated or oxolated, a $C_{1-6}$ alkoxy which may be halogenated or oxolated, a $C_{1-6}$ acylamino which may be halogenated or oxolated, a N—($C_{1-6}$ alkyl)$C_{1-6}$ acylamino, a $C_{1-6}$ acyl which may be halogenated or oxolated, a $C_{1-6}$ alkylamino, a di-$C_{1-6}$ alkylamino, a $C_{1-6}$ alkenyl which may be halogenated or oxolated, a $C_{1-6}$ alkynyl which may be halogenated or oxolated, a $C_{1-6}$ alkyloxycarbonyl, carbamoyl, carboxy, a $C_{1-6}$ alkylsulfonylamide which may be halogenated or oxolated, a $C_{1-6}$ alkylthio which may be halogenated or oxolated, a $C_{1-6}$ alkylsulfinyl which may be halogenated or oxolated, amino, hydroxyl, a halogen and nitrile, or a salt thereof.

* * * * *